(12) United States Patent
Ashkenazi et al.

(10) Patent No.: US 6,764,679 B2
(45) Date of Patent: Jul. 20, 2004

(54) ANTIBODIES TO DCR3 POLYPEPTIDE, A TNFR HOMOLOG

(75) Inventors: Avi J. Ashkenazi, San Mateo, CA (US); David Botstein, Belmont, CA (US); Kelly H. Dodge, San Mateo, CA (US); Audrey Goddard, San Francisco, CA (US); Austin L. Gurney, Belmont, CA (US); Kyung Jin Kim, Los Altos, CA (US); David A. Lawrence, San Francisco, CA (US); Robert Pitti, El Cerrito, CA (US); Margaret A. Roy, San Francisco, CA (US); Daniel B. Tumas, Orinda, CA (US); William I. Wood, Hillsborough, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/896,096

(22) Filed: Jun. 28, 2001

(65) Prior Publication Data

US 2002/0061559 A1 May 23, 2002

Related U.S. Application Data

(63) Continuation of application No. 09/157,289, filed on Sep. 18, 1998, now abandoned.
(60) Provisional application No. 60/059,288, filed on Sep. 18, 1997, and provisional application No. 60/094,640, filed on Jul. 30, 1998.

(51) Int. Cl.⁷ .................... C07K 16/28; C07K 16/30; C12N 15/13
(52) U.S. Cl. ................ 424/130.1; 424/133.1; 424/138.1; 424/141.1; 424/143.1; 530/387.1; 530/387.3; 530/387.7; 530/387.9; 530/388.22; 530/389.1; 530/389.7; 530/350; 530/388.15; 435/69.7
(58) Field of Search ............... 435/69.7, 326, 435/328, 330, 331, 334, 358, 252.3, 254.2; 424/133.1, 138.1, 141.1, 143.1, 130.1; 530/350, 387.1, 387.3, 387.9, 388.2, 388.15, 388.22, 389.1, 389.7, 388.8; 536/23.5

(56) References Cited

U.S. PATENT DOCUMENTS

| | | | |
|---|---|---|---|
| 4,179,337 A | 12/1979 | Davis et al. | |
| 4,301,144 A | 11/1981 | Iwashita et al. | |
| 4,399,216 A | 8/1983 | Axel et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,676,980 A | 6/1987 | Segal et al. | |
| 4,736,866 A | 4/1988 | Leder et al. | |
| 4,791,192 A | 12/1988 | Nakagawa et al. | |
| 4,816,567 A | 3/1989 | Cabilly et al. | |
| 4,870,009 A | 9/1989 | Evans et al. | |
| 4,946,778 A | * 8/1990 | Ladner et al. | |
| 5,010,182 A | 4/1991 | Brake et al. | |
| 5,364,934 A | 11/1994 | Drayna et al. | |
| 5,447,851 A | 9/1995 | Beutler et al. | |
| 5,885,800 A | 3/1999 | Emery et al. | |
| 6,297,367 B1 | * 10/2001 | Tribouley | ................. 536/23.5 |
| 6,599,716 B1 | 7/2003 | Hsu | |
| 2002/0068064 A1 | 6/2002 | Shen-Chih et al. | |
| 2002/0150583 A1 | 10/2002 | Gentz et al. | |

FOREIGN PATENT DOCUMENTS

| | | |
|---|---|---|
| DE | 19809978 | 9/1999 |
| EP | 0003089 A1 | 7/1979 |
| EP | 036776 A2 | 9/1981 |
| EP | 073657 | 3/1983 |
| EP | 117058 A2 | 8/1984 |
| EP | 117060 A2 | 8/1984 |
| EP | 307247 B1 | 3/1989 |
| EP | 362179 A2 | 4/1990 |
| EP | 417563 B1 | 3/1991 |
| EP | 861850 | 9/1998 |
| GB | 2211504 | 7/1989 |
| WO | WO 87/05330 | 9/1987 |
| WO | WO 89/05859 | 6/1989 |
| WO | WO 90/13646 | 11/1990 |
| WO | WO 91/00360 | 1/1991 |
| WO | WO 92/20373 | 11/1992 |
| WO | WO 93/08829 | 5/1993 |
| WO | WO 97/23614 | 7/1997 |
| WO | WO 97/25428 | 7/1997 |
| WO | WO 98/30694 | 7/1998 |
| WO | WO 98/32856 | 7/1998 |
| WO | WO 99/04001 | 1/1999 |
| WO | WO 99/07738 | 2/1999 |
| WO | WO 99/11791 | 3/1999 |
| WO | WO 99/14330 | 3/1999 |
| WO | WO 99/26977 | 6/1999 |
| WO | WO 99/31128 | 6/1999 |
| WO | WO 99/50413 | 7/1999 |
| WO | WO 00/32221 | 6/2000 |
| WO | WO 00/52028 | 9/2000 |
| WO | WO 00/53758 | 9/2000 |
| WO | WO 00/58465 | 10/2000 |
| WO | WO 00/58466 | 10/2000 |

OTHER PUBLICATIONS

U.S. patent application Ser. No. 60/035,496, filed Jan. 14, 1997.

U.S. patent application Ser. No. 60/035,722, filed Jan. 28, 1997.

U.S. patent application Ser. No. 60/037,829, filed Feb. 5, 1997.

U.S. patent application Ser. No. 60/079,856, Dou et al., filed Mar. 30, 1998.

(List continued on next page.)

*Primary Examiner*—Lorraine Spector
*Assistant Examiner*—Claire M. Kaufman
(74) *Attorney, Agent, or Firm*—Diane L. Marschang

(57) ABSTRACT

A TNFR homolog, identified as DcR3, is provided. Nucleic acid molecules encoding DcR3, chimeric molecules and antibodies to DcR3 are also provided.

33 Claims, 13 Drawing Sheets

OTHER PUBLICATIONS

U.S. patent application Ser. No. 60/086,074, Dou et al., filed May 20, 1998.
U.S. patent application Ser. No. 60/099,643, Dou et al., filed Sep. 9, 1998.
U.S. patent application Ser. No. 60/112,577, Dou et al., filed Dec. 17, 1998.
U.S. patent application Ser. No. 60/112,703, Dou et al., filed Dec. 18, 1998.
U.S. patent application Ser. No. 60/112,933, Dou et al., filed Dec. 18, 1998.
U.S. patent application Ser. No. 60/113,407, Dou et al., filed Dec. 22, 1998.
Altschul et al., "Local alignment statistics" *Methods in Enzymology* 266:460–480 (1996).
Amakawa et al., "The Hodgkin Disease Antigen CD30 is Crucial for Antigen–induced Death of Developing T Cells" *Cold Spring Harbor Laboratory Symposium on Programmed Cell Death* (Abstr. No. 10) (1995).
Anderson et al., "A homologue of the TNF receptor and its ligand enhance T–cell growth and dendritic–cell function" *Nature* 390 (6656): 175–179 (Nov. 13, 1997).
Anderson, W.F., "Human gene therapy" *Science* 256 (5058): 808–813 (May 8, 1992).
Aplin and Wriston, "Preparation, Properties, and Applications of Carbohydrate Conjugates of Proteins and Lipids" *CRC Crit. Rev. Biochem.* 10(4): 259–306 (1981).
Arase et al., "Fas–mediated cytotoxicity by freshly isolated natural killer cells" *Journal of Experimental Medicine* 181(3): 1235–1238 (Mar. 1, 1995).
Ashkenazi and Chamow, "Immunoadhesins: An Alternative to Human Monoclonal Antibodies". *Methods: A Companion to Methods in Enzymology* 8:104–115 (1995).
Ashkenazi et al., "Protection Against Endotoxic Shock by a Tumor Necrosis Factor Receptor Immunoadhesin" *Proc. Natl. Acad. Sci.* 88:10535–10539 (1991).
Bai et al., "Overexpression of M68/DcR3 in human gastrointestinal tract tumors independent of gene amplification and its location in a four–gene cluster" *Proc. Natl. Acad. Sci.* 97:1230–1235 (2000).
Banner et al., "Crystal Structure of the Soluble Human 55 kd TNF Receptor–Human TNFβ Complex: Implications for TNF Receptor Activation" *Cell* 73: 431–445 (1993).
Bodmer et al., "TRAMP, a Novel Apoptosis–Mediating Receptor with Sequence Homology to Tumor Necrosis Factor Receptor 1 and Fas(Apo–1/CD95)" *Immunity* 6:79–88 (1997).
Boerner et al., "Production of Antigen–Specific Human Monoclonal Antibodies From In Vitro–Primed Human Splenocytes" *The Journal of Immunology* 147(1): 86–95 (1991).
Bolivar et al., "Construction and Characterization of New Cloning Vehicles. II. A Multipurpose Cloning System" *Gene* 2:95–113 (1977).
Bradley, "Production and Analysis of Chimaeric Mice" *Teratocarcinomas and Embryonic Stem Cells: A Practical Approach*, E. J. Robertson, ed., IRL, Oxford, Chapter 5, pp. 113–151 (1987).
Brockhaus et al., "Identification of two types of tumor necrosis factor receptors on human cell lines by monoclonal antibodies" *Proc. Natl. Acad. Sci. USA* 87:3127–3131 (1990).

Brodeur et al., "Mouse–Human Myeloma Partners for the Production of Heterohybridomas" *Monoclonal Antibody Production Techniques and Applications*, New York: Marcel Dekker, Inc. pp. 51–63 (1987).
Brojatsch et al., "CAR1, a TNFR–Related Protein, Is a Cellular Receptor for Cytopathic Avian Leukosis–Sarcoma Viruses and Mediates Apoptosis" *Cell* 87:845–855 (1996).
Carter et al., "Improved oligonucleotide site–directed mutagenesis using M13 vectors" *Nucl. Acids Res.* 13(12): 4431–4443 (1985).
Chang et al., "Phenotypic Expression in *E. coli* of a DNA Sequence Coding for Mouse Dihydrofolate Reductase" *Nature* 275:617–624 (Oct. 19, 1978).
Chicheportiche et al., "TWEAK, a new secreted ligand in the tumor necrosis factor family that weakly induces apoptosis" *Journal of Biological Chemistry* 272(51): 32401–32410 (1997).
Chinnaiyan et al., "Signal Transduction by DR3, a Death Domain–Containing Receptor Related to TNFR–1 and CD95" *Science* 274: 990–992 (1996).
Chothia, "The Nature of the Accessible and Buried Surfaces in Proteins" *Journal Mol. Biol.* 105:1–14 (1976).
Cole et al., "The EBV–Hybridoma Technique and Its Application to Human Lung Cancer" *Monoclonal Antibodies and Cancer Therapy*, New York: Alan R. Liss, Inc. pp. 77–96 (1985).
Creighton, "Protein Biosynthesis" *Proteins: Structures and Molecular Principles*, San Francisco: W.H. Freeman & Co. pp. 79–86 (1983).
David et al., "Protein Iodination with Solid State Lactoperoxidase" *Biochemistry* 13(5): 1014–1021 (1974).
Dealtry at al., "DNA Fragmentation and Cytotoxicity Caused by Tumor Necrosis Factor is Enhanced by Interferon–γ" *European Journal of Immunology* 17:689–693 (1987).
deBoer et al., "The TAC Promoter: A functional Hybrid Derived From the TRP and LAC Promoters" *Proc. Natl. Acad. Sci. USA* 80:21–25 (1983).
Deutscher, M., "Rethinking your purification procedure" *Methods in Enzymology* 182:779–780 (1990).
Dhein et al., "Autocrine T–cell suicide mediated by APO–1/(Fas/CD95)" *Nature* 373(6513): 438–441 (Feb. 2, 1995).
Dzau et al., "Gene therapy for cardiovascular disease" *Trends in Biotechnology* 11:205–210 (1993).
Edge et al., "Deglycosylation of glycoproteins by trifluoromethanesulfonic acid" *Analytical Biochemistry* 118: 131–137 (1981).
Evan et al., "Isolation of Monoclonal Antibodies Specific for Human c–myc Proto–Oncogene Product" *Molecular & Cellular Biology* 5:3610–3616 (1985).
Field et al., "Purification of a RAS–Responsive Adenylyl Cyclase Complex from *Saccharomyces cerevisiae* by Use of an Epitope Addition Method" *Molecular & Cellular Biology* 8:2159–2165 (1988).
Gelb et al., "Pycnodysostosis: Refined Linkage and Radiation Hybrid Analyses Reduce the Critical Region to 2 cM at lq21 and Map Two Candidate Genes" *Human Genet.* 98: 141–144 (1996).
Gelmini et al., "Quantitative polymerase chain reaction–based homogeneous assay with fluorogenic probes to measure c–erbB–2 oncogene amplification" *Clinical Chemistry* 43(5): 752–758 (May 1997).

Gething and Sambrook, "Cell–surface Expression of Influenza Haemagglutinin from a Cloned DNA Copy of the RNA Gene" *Nature* 293: 620–625 (Oct. 22, 1981).

Goding, "Production of Monoclonal Antibodies" *Monoclonal Antibodies: Principles and Practice*, Academic Press, pp. 59–103 (1986).

Goeddel et al., "Direct Expression in *Escherichia coli* of a DNA Sequence Coding for Human Growth Hormone" *Nature* 281:544–548 (Oct. 18, 1979).

Goeddel et al., "Synthesis of Human Fibroblast Interferon by *E. coli*" *Nucleic Acids Research* 8(18): 4057–4074 (1980).

Goodwin et al., "Molecular cloning and expression of the type 1 and type 2 murine receptors for tumor necrosis factor" *Molecular & Cellular Biology* 11:3020–3026 (1991).

Graham and van der Eb, "A New Technique for the Assay of Infectivity of Human Adenovirus 5 DNA" *Virology* 52:456–467 (1973).

Graham et al., "Characteristics of a Human Cell Line Transformed by DNA from Human Adenovirus Type 5" *J. Gen. Virol.* 36:59–74 (1977).

Gruss and Dower, "Tumor Necrosis Factor Ligand Superfamily: Involvement in the Pathology of Malignant Lymphomas" *Blood* 85:3378–3404 (1995).

Hahne et al., "Melanoma cell expression of Fas(Apo–1/CD95) ligand: implications for tumor immume escape" *Science* 274 (5291): 1363–1366 (Nov. 22, 1996).

Hale et al., "Demonstration of in vitro and in vivo efficacy of two biologically active human soluble TNF receptors expressed in *E. coli*" *J. Cell. Biochem.* (abstract only Supplement 15F; P 424) pp. 113 (1991).

*Handbook of Monoclonal Antibodies*, Ferrone et al. eds., Park Ridge, NJ: Noyes Publications, pp. 302–359 and Chapter 22 (1985).

Hess et al., "Cooperation of Glycolytic Enzymes" *Advances in Enzyme Regulation*, George Weber, New York: Pergamon Press vol. 7:149–167 (1968).

Hitzeman et al., "Isolation and Characterization of the Yeast 3–Phosphoglycerokinase Gene (PGK) by an Immunological Screening Technique" *Journal of Biological Chemistry* 255(24): 12073–12080 (Dec. 25, 1980).

Hohmann et al., "Two different cell types have different major receptors for human tumor necrosis factor (TNFα)" *Journal of Biological Chemistry* 264(25): 14927–14934 (1989).

Holland and Holland, "Isolation and Identification of Yeast Messenger Ribonucleic Acids Coding for Enolase, Glyceraldehyde–3–phosphate Dehydrogenase, and Phosphoglycerate Kinase" *Biochemistry* 17(23): 4900–4907 (1978).

Holmes et al., "Structure and Functional Expression of a Human Interleukin–8 Receptor" *Science* 253(5025): 1278–1280 (1991).

Hoogenboom and Winter, "By–passing immunisation: human antibodies from synthetic repertoires of germline $V_H$ gene segments rearranged in vitro" *J. Mol. Biol.* 227:381–388 (1992).

Hopp et al., "A Short Polypeptide Marker Sequence Useful for Recombinant Protein Identification and Purification" *Bio/Technology* 6:1204–1210 (1988).

Hsiao and Carbon, "High–frequency Transformation of Yeast by Plasmids Containing the Cloned Yeast Arg4 Gene" *Proc. Natl. Acad. Sci. USA* 76:3829–3833 (1979).

Hunter et al., "Preparation of Iodine 131 Labelled Human Growth Hormone of High Specific Activity" *Nature* 194: 495–496 (1962).

Itoh et al., "The polypeptide encoded by the cDNA for human cell surface antigen Fas can mediate apoptosis" *Cell* 66: 233–243 (1991).

Johnson et al., "Expression and Structure of the Human NGF Receptor" *Cell* 47:545–554 (1986).

Jones et al., "Replacing the Complementarity–determining Regions in a Human Antibody with Those From a Mouse" *Nature* 321:522–525 (May 29, 1986).

Jones, E., "Proteinase Mutants of *Saccharomyces Cerevisiae*" *Genetics* 85(1): 23–33 (1977).

Keown et al., "Methods for Introducing DNA into Mammalian Cells" *Methods in Enzymology* 185:527–537 (1990).

Kingsman et al., "Replication in *Saccharomyces Cerevisiae* of Plasmid pBR313 Carrying DNA from the Yeast trp1 Region" *Gene* 7:141–152 (1979).

Kitson et al., "A Death–Domain–Containing Receptor that Mediates Apoptosis" *Nature* 384:372–375 (1996).

Kohler and Milstein, "Continuous Cultures of Fused Cells Secreting Antibody of Predefined Specificity" *Nature* 256: 495–497 (Aug. 7, 1975).

Kohno et al., "A second tumor necrosis factor receptor gene product can shed a naturally occurring tumor necrosis factor inhibitor" *Proc. Natl. Acad. Sci. USA* 87:8331–8335 (1990).

Kozbor et al., "A Human Hybrid Myeloma for Production of Human Monoclonal Antibodies" *The Journal of Immunology* 133(6): 3001–3005 (1984).

Krammer et al., "Regulation of Apoptosis in the Immune System" *Curr. Op. Immunol.* 6:279–289 (1994).

Kwon et al., "Manipulation of T cell costimulatory and inhibitory signals for immunotherapy of prostate cancer" *Proc. Natl. Acad. Sci. USA* 94(15): 8099–8103 (Jul. 22, 1997).

Lacey et al., "Osteoprotegerin ligand is a cytokine that regulates osteoclast differentiation and activation" *Cell* 93(2): 165–176 (Apr. 17, 1998).

Leach et al., "Enhancement of antitumor immunity by CTLA–4 blockade" *Science* 271(5256): 1734–1736 (Mar. 22, 1996).

Lewis et al., "Cloning and expression of cDNAs for two distinct murine tumor necrosis factor receptors demonstrate one receptor is species specific" *Proc. Natl. Acad. Sci. USA* 88:2830–2834 (1991).

Li et al., "Targeted mutation of the DNA methyltransferase gene results in embryonic lethality" *Cell* 69:915–926 (1992).

Loetscher et al., "Molecular Cloning and Expression of the Human 55 kd Tumor Necrosis Factor Receptor" *Cell* 61:351–359 (1990).

Lutz–Freyermuth et al., "Quantitative Determination That One of Two Potential RNA–binding Domains of the A Protein Component of the U1 Small Nuclear Ribonucleoprotein Complex Binds with High Affinity to Stem–loop II of U1 RNA" *Proc. Natl. Acad. Sci. USA* 87:6393–6397 (1990).

Mallett et al., "Characterization of the MRC OX40 Antigen of Activated CD4 Positive T Lymphocytes—a Molecule Related to Nerve Growth Factor Receptor" *EMBO Journal* 9:1063–1068 (1990).

Mansour et al., "Disruption of the Proto–oncogene int–2 in Mouse Embryo–derived Stem Cells: a General Strategy for Targeting Mutations to Non–selectable Genes" *Nature* 336:348–352 (1988).

Mantei et al., "Rabbit β–globin mRNA Production in Mouse L Cells Transformed with Cloned Rabbit β–globin Chromosomal DNA" *Nature* 281:40–46 (Sep. 6, 1979).

Marks et al., "By–passing immunization: human antibodies from V–gene libraries displayed on phage" *J. Mol. Biol.* 222:581–597 (1991).

Marsters et al., "Activation of Apoptosis by Apo–2 Ligand is Independent of FADD but Blocked by CrmA" *Current Biology* 6(6): 750–752 (1996).

Marsters et al., "Apo–3, a New Member of the Tumor Necrosis Factor Receptor Family, Contains a Death Domain and Activates Apoptosis and NF–κB" *Curr. Biol.* 6(12):1669–1676 (1996).

Marsters et al., "Herpesvirus Entry Mediator, A Member of the Tumor Necrosis Factor (TNFR) Family, Interacts with Members of the TNFR–associated Factor Family and Activates the Transcription Factors NF–κB and AP–1" *Journal of Biological Chemistry* 272(22): 14029–14032 (1997).

Marsters et al., "Identification of a ligand for the death–domain–containing receptor Apo3" *Current Biology* 8(9): 525–528 (1998).

Martin et al., "GAP Domains Responsible for Ras p21–Dependent Inhibition of Muscarinic Atrial $K^+$ Channel Currents" *Science* 255: 192–194 (1992).

Mather, J.P., "Establishment and Characterization of Two Distinct Mouse Testicular Epithelial Cell Lines" *Biol. Reprod.* 23:243–252 (1980).

Mauri et al., "LIGHT, a new member of the TNF superfamily, and lymphotoxin α are ligands for herpesvirus entry mediator" *Immunity* 8(1): 21–30 (Jan. 1998).

Medvedev et al., "Regulation of Fas and Fas–ligand expression in NK cells by cytokines and the involvement of Fas–ligand in NK/LAK cell–mediated cytotoxicity" *Cytokine* 9(6): 394–404 (Jun. 1997).

Merrifield, R.B., "Solid Phase Peptide Synthesis. I. The Synthesis of a Tetrapeptide" *J. Am. Chem. Soc.* 85:2149–2154 (1963).

Milstein et al., "Hybrid Hybridomas and Their Use in Immunohistochemistry" *Nature* 305:537–540 (1983).

Montgomery et al., "Herpes Simplex Virus–1 Entry into Cells Mediated by a Novel Member of the TNF/NGF Receptor Family" *Cell* 87(3): 427–436 (1996).

Moretta, A., "Molecular mechanisms in cell–mediated cytotoxicity" *Cell* 90(1): 13–18 (Jul. 11, 1997).

Munson et al., "LIGAND: A Versatile Computerized Approach for Characterization of Ligand–Binding Systems" *Analytical Biochemistry* 107:220–239 (1980).

Nagata and Golstein, "The Fas Death Factor" *Science* 267: 1449–1456 (1995).

Nagata, S., "Apoptosis by Death Factor" *Cell* 88:355–365 (1997).

Nophar et al., "Soluble forms of tumor necrosis factor receptors (TNF–Rs). The cDNA for the type I TNF–R, cloned using amino acid sequence data of its soluble form, encodes both the cell surface and a soluble form of the receptor" *EMBO Journal* 9:3269–3278 (1990).

Nygren, H., "Conjugation of Horseradish Peroxidase to Fab Fragments with Different Homobifunctional and Heterobifunctional Cross–Linking Reagents" *The Journal of Histochemistry and Cytochemistry* 30(5): 407–412 (1982).

Otsuki et al., "Over–expression of the decoy receptor 3 (DcR3) gene in peripheral blood mononuclear cells (PBMC) derived from silicosis patients" *Clin. Exp. Immunl.* 119:323–327 (2000).

Paborsky et al., "Mammalian Cell Transient Expression of Tissue Factor for the Production of Antigen" *Protein Eng.* 3(6): 547–553 (1990).

Pain et al., "Preparation of Protein A–Peroxidase Monoconjugate Using a Heterobifunctional Reagent, and its Use in Enzyme Immunoassays" *Journal of Immunological Methods* 40:219–230 (1981).

Pan et al., "An Antagonist Decoy Receptor and a Death–domain Containing Receptor for TRAIL" *Science* 277:815–818 (1997).

Pan et al., "The Receptor for the Cytotoxic Ligand TRAIL" *Science* 276:111–113 (1997).

Peetre et al., "A tumor necrosis factor binding protein is present in human biological fluids" *European Journal of Haematology* 41: 414–419 (1988).

Pennica et al., "Human Tumour Necrosis Factor: Precursor Structure, Expression and Homology to Lymphotoxin" *Nature* 312:724–729 (1984).

Pitti et al., "Induction of Apoptosis by Apo–2 Ligand, a New Member of the Tumor Necrosis Factor Cytokine Family" *Journal of Biological Chemistry* 271: 12687–12690 (1996).

Presta, L., "Antibody Engineering" *Curr. Op. Struct. Biol.* 2:593–596 (1992).

Radeke et al., "Gene transfer and molecular cloning of the rat nerve growth factor receptor" *Nature* 325:593–597 (1987).

Riechmann et al., "Reshaping Human Antibodies for Therapy" *Nature* 332: 323–327 (Mar. 24, 1988).

Ruppert et al., "Cloning and Expression of Human $TAF_{II}250$: a TBP–associated Factor Implicated in Cell–cycle Regulation" *Nature* 362:175–179 (1993).

Schall et al., "Molecular Cloning and Expression of a Receptor for Human Tumor Necrosis Factor" *Cell* 61:361–370 (1990).

Schmid et al., "DNA Fragmentation: Manifestation of Target Cell Destruction Mediated by Cytotoxic T–cell Lines, Lymphotoxin–secreting Helper T–cell Clones, and Cell–free Lymphotoxin–containing Supernatant" *Proc. Natl. Acad. Sci. USA* 83:1881–1885 (1986).

Seckinger et al., "Purification and biologic characterization of a specific tumor necrosis factor α Inhibitor" *Journal of Biological Chemistry* 264:11966–11973 (1989).

Shaw et al., "A General Method for the Transfer of Cloned Genes to Plant Cells" *Gene* 23:315–330 (1983).

Sheridan et al., "Control of TRAIL–Induced Apoptosis by a Family of Signaling and Decoy Receptors" *Science* 277:818–821 (1997).

Simonet et al., "Osteoprotegerin: A Novel Secreted Protein Involved in the Regulation of Bone Density" *Cell* 89:309–319 (1997).

Skinner et al., "Use of the Glu–Glu–Phe C–terminal Epitope for Rapid Purification of the Catalytic Domain of Normal and Mutant ras GTPase–activating Proteins" *Journal of Biological Chemistry* 266:14163–14166 (1991).

Smith et al., "A Receptor for Tumor Necrosis Factor Defines an Unusual Family of Cellular and Viral Proteins" *Science* 248:1019–1023 (1990).

Smith et al., "Cardiac Glycoside–Specific Antibodies in the Treatment of Digitalis Intoxication" *Antibodies in Human Diagnosis and Therapy* pp. 365–389 (1977).

Smith et al., "T2 Open reading frame from the shope fibroma virus encodes a soluble form of the TNF receptor" *Biochem. & Biophys. Res. Comm.* 176:335–342 (1991).

Sojar et al., "A Chemical Method for the Deglycosylation of Proteins" *Archives of Biochemistry & Biophysics* 259(1): 52–57 (1987).

Sompayrac et al., "Efficient infection of monkey cells with DNA of simian virus 40" *Proc. Natl. Acad. Sci. USA* 78(12): 7575–7578 (Dec. 1981).

Stamenkovic et al., "A B–lymphocyte activation molecule related to the nerve growth factor receptor and induced by cytokines in carcinomas" *EMBO Journal* 8(5): 1403–1410 (1989).

Stinchcomb et al., "Isolation and Characterisation of a Yeast Chromosomal Replicator" *Nature* 282:39–43 (Nov. 1, 1979).

Strand et al., "Lymphocyte apoptosis induced by CD95 (APO–1/Fas) ligand–expressing tumor cells—a mechanism of immune evasion?" *Nature Medicine* 2(12): 1361–1366 (Dec. 1996).

Suda et al., "Molecular Cloning and Expression of the Fas Ligand, a Novel Member of the Tumor Necrosis Factor Family" *Cell* 75: 1169–1178 (1993).

Suresh et al., "Bispecific Monoclonal Antibodies from Hybrid Hybridomas" *Methods in Enzymology* 121: 210–228 (1986).

Takao et al., "Novel DNA Polymorphism in the Mouse Tumor Necrosis Factor Receptors Type 1 and Type 2" *Immunogenetics* 37: 199–203 (1993).

Thimmappaya et al., "Adenovirus VAI RNA is required for efficient translation of viral mRNAs at late times after infection" *Cell* 31(3 Pt 2): 543–551 (Dec. 1982).

Thomas and Capecchi, "Site–Directed Mutagenesis by Gene Targeting in Mouse Embryo–Derived Stem Cells" *Cell* 51:503–512 (1987).

Thomas, P., "Hybridization of Denatured RNA and Small DNA Fragments Transferred to Nitrocellulose" *Proc. Natl. Acad. Sci. USA* 77(9): 5201–5205 (Sep. 1980).

Thotakura and Bahl, "Enzymatic Deglycosylation of Glycoproteins" *Meth. Enzymol.* 138:350–359 (1987).

Traunecker et al., "Bispecific Single Chain Molecules (Janusins) Target Cytotoxic Lymphocytes on HIV Infected Cells" *EMBO Journal* 10(12): 3655–3659 (1991).

Tschumper and Carbon, "Sequence of a Yeast DNA Fragment Containing a Chromosomal Replicator and the TRP1 Gene" *Gene* 10:157–166 (1980).

Upton et al., "Myxoma virus expresses a secreted protein with homology to the tumor necrosis factor receptor gene family that contributes to viral virulence" *Virology* 184: 370–382 (1991).

Upton et al., "Tumorigenic poxviruses: genomic organization and DNA sequence of the telomeric region of the shope fibroma virus genome" *Virology* 160:20–30 (1987).

Urlaub and Chasin, "Isolation of Chinese Hamster Cell Mutants Deficient in Dihydrofolate Reductase Activity" *Proc. Natl. Acad. Sci. USA* 77(7): 4216–4220 (Jul. 1980).

Van Solingen et al., "Fusion of Yeast Spheroplasts" *J. Bact.* 130:946–947 (1977).

Verhoeyen et al., "Reshaping Human Antibodies: Grafting an Antilysozyme Activity" *Science* 239:1534–1536 (Mar. 25, 1988).

Wagner et al., "Transferrin–polycation conjugates as carriers for DNA uptake into cells" *Proc. Natl. Acad. Sci.* 87:3410–3414 (1990).

Welcher et al., "Nerve growth factor binding domain of the nerve growth factor receptor" *Proc. Natl. Acad. Sci. USA* 88:159–163 (1991).

Wells et al., "Cassette Mutagenesis: an Efficient Method for Generation of Multiple Mutations at Defined Sites" *Gene* 34(2–3): 315–323 (1985).

Wells et al., "Importance of hydrogen–bond formation in stabilizing the transition state of subtilisin" *Philos. Trans. R. Soc. London Ser A* 317: 415–423 (1986).

Wiley et al., "Identification and Characterization of a New Member of the TNF Family that Induces Apoptosis" *Immunity* 3: 673–682 (1995).

Wong et al., "TRANCE Is a Novel Ligand of the Tumor Necrosis Factor Receptor Family That Activates c–Jun N–terminal Kinase in T Cells" *Journal of Biological Chemistry* 272(40): 25190–25194 (Oct. 3, 1997).

Wu et al., "Receptor–mediated in vitro gene transformation by a soluble DNA carrier system" *Journal of Biological Chemistry* 262(10): 4429–4432 (1987).

Yan and Chao, "Disruption of Cysteine–rich repeats of the p75 nerve growth factor receptor leads to loss of ligand binding" *Journal of Biological Chemistry* 266: 12099–12104 (1991).

Yonehara et al., "A cell–killing monoclonal antibody (anti–Fas) to a cell surface antigen co–downregulated with the receptor of tumor necrosis factor" *Journal of Experimental Medicine* 169: 1747–1756 (1989).

Yu, K. et al., "A newly identified member of tumor necrosis factor receptor superfamily (TR6) suppresses light–mediated apoptosis" *J. Biol. Chemistry* 274(20): 13733–13736 (1999).

Zamecnik et al., "Inhibition of replication and expression of human T–cell lymphotropic virus type III in cultured cells by exogenous synthetic oligonucleotides complementary to viral RNA" *Proc. Natl. Acad. Sci.* 83: 4143–4146 (1986).

Zheng et al., "Induction of Apoptosis in Mature T Cells by Tumor Necrosis Factor" *Nature* 377: 348–351 (1995).

Zola, "Using Monoclonal Antibodies: Soluble Antigens" *Monoclonal Antibodies: A Manual of Techniques*, CRC Press, Chapter 6, pp. 147–158 (1987).

Zoller and Smith, "Oligonucleotide–directed Mutagenesis Using M13–derived Vectors: An Efficient and General Procedure for the Production of Point Mutations in Any Fragment of DNA" *Nucl. Acids Res.* 10(20): 6487–6500 (1982).

U.S. patent application Ser. No. 09/518,931, R. Gentz et al., filed Mar. 3, 2000.

U.S. patent application Ser. No. 09/006,352, R. Gentz et al., filed Jan. 13, 1998.

U.S. patent application Ser. No. 60/303,224, R. Gentz et al., filed Jul. 6, 2001.

U.S. patent application Ser. No. 60/252,131, R. Gentz et al., filed Nov. 21, 2000.

U.S. patent application Ser. No. 60/227,598, R. Gentz et al., filed Aug. 25, 2000.

U.S. patent application Ser. No. 60/168,235, R. Gentz et al., filed Dec. 1, 1999.

U.S. patent application Ser. No. 60/146,371, R. Gentz et al., filed Aug. 2, 1999.

U.S. patent application Ser. No. 60/131,964, R. Gentz et al., filed Apr. 30, 1999.
U.S. patent application Ser. No. 60/131,270, C. Watanabe et al., filed Apr. 27, 1999.
U.S. patent application Ser. No. 60/124,092, R. Gentz et al., filed Mar. 12, 1999.
U.S. patent application Ser. No. 60/121,774, R. Gentz et al., filed Mar. 4, 1999.
U.S. patent application Ser. No. 60/035,496, W. Ying–Fei et al., filed Jan. 14, 1997.

Bai et al. "Overexpression of M68/DcR3 in human gastrointestinal tract tumors independent of gene amplification and its location in a four–gene cluster." PNAS, vol. 97, pp. 1230–1235 (2000).

Otsuki et al. "Over–expression of the decoy receptor 3 (DcR3) gene in peripheral blood mononuclear cells (PBMC) derived from silicosis patients." Clinical and Experimental Immunology, vol. 119, No. 2, pp. 323–327 (2000).

* cited by examiner

MRALEGPGLSLLCLVLALPALLPVPAVRGVAETPTYPWRDAETGERLVCAQCPPGTFVQR
PCRRDSPTTCGPCPPRHYTQFWNYLERCRYCNVLCGEREESARACHATHNRACRCRTGFF
AHAGFCLEHASCPPGAGVIAPGTPSQNTQCQPCPPGTFSASSSSSEQCQPHRNCTALGLA
LNVPGSSSHDTLCTSCTGFPLSTRVPGAEECERAVIDFVAFQDISIKRLQRLLQALEAPE
GWGPTPRAGRAALQLKLRRRLTELLGAQDGALLVRLLQALRVARMPGLERSVRERFLPVH

FIG. 1

TCCGCAGGCGGACCGGGGGCAAAGGAGGTGGCATGTCGGTCAGGCACAGCAGGGTCCTGT
GTCCGCGCTGAGCCGCGCTCTCCCTGCTCCAGCAAGGACC
><Met (trans-1-s, dir=f, res=1)>
ATGAGGGCGCTGGAGGGGCCAGGCCTGTCGCTGCTGTGCCTGGTGTTGGCGCTGCCTGCC
CTGCTGCCGGTGCCGGCTGTACGCGGAGTGGCAGAAACACCCACCTACCCCTGGCGGGAC
GCAGAGACAGGGGAGCGGCTGGTGTGCGCCCAGTGCCCCCCAGGCACCTTTGTGCAGCGG
CCGTGCCGCCGAGACAGCCCCACGACGTGTGGCCCGTGTCCACCGCGCCACTACACGCAG
TTCTGGAACTACCTGGAGCGCTGCCGCTACTGCAACGTCCTCTGCGGGGAGCGTGAGGAG
GAGGCACGGGCTTGCCACGCCACCCACAACCGTGCCTGCCGCTGCCGCACCGGCTTCTTC
GCGCACGCTGGTTTCTGCTTGGAGCACGCATCGTGTCCACCTGGTGCCGGCGTGATTGCC
CCGGGCACCCCCAGCCAGAACACGCAGTGCCAGCCGTGCCCCCCAGGCACCTTCTCAGCC
AGCAGCTCCAGCTCAGAGCAGTGCCAGCCCCACCGCAACTGCACGGCCCTGGGCCTGGCC
CTCAATGTGCCAGGCTCTTCCTCCCATGACACCCTGTGCACCAGCTGCACTGGCTTCCCC
CTCAGCACCAGGGTACCAGGAGCTGAGGAGTGTGAGCGTGCCGTCATCGACTTTGTGGCT
TTCCAGGACATCTCCATCAAGAGGCTGCAGCGGCTGCTGCAGGCCCTCGAGGCCCCGGAG
GGCTGGGGTCCGACACCAAGGGCGGGCCGCGCGGCCTTGCAGCTGAAGCTGCGTCGGCGG
CTCACGGAGCTCCTGGGGGCGCAGGACGGGGCGCTGCTGGTGCGGCTGCTGCAGGCGCTG
CGCGTGGCCAGGATGCCCGGGCTGGAGCGGAGCGTCCGTGAGCGCTTCCTCCCTGTGCAC
TGATCCTGGCCCCCTCTTATTTATTCTACATCCTTGGCACCCCACTTGCACTGAAAGAGG
CTTTTTTTTAAATAAGAAGAAATGAGGTTTNTTAAAAAAAAAAAAAAAAAAAAAA

FIG. 2

GCCGAGACAGCCCCACGACGTGTGGCCCGTGTCCACCGCGCCACTACACG
CAGTTCTGGAANTAACTGGAGCNCTGCCGCTACTGNAACGTCCTCTGNGG
GGAGCGTGAGGAGGAGGCACGGGCTTGCCACGCCACCCACAACCGTGCCT
GCCGCTGCCGCACCGGCTTCTTCGCGCACGCTGGTTTCTGCTTGGAGCAC
GCATCGTGTCCACCTGGTGCCGGCGTGATTGCCCCGGGCACCCCCAGCCA
GAACACGCAGTGCCTAGCCGTGCCCCCAGGCACCTTCTCAGCCAGCAGC
TCCAGCTCAGAGCAGTGCCAGCCCCACCGCAACTGCACGGCCCTGGGCCT
GGCCCTCAATGTGCCAGGCTCTTCCTCCCATGACACCCTGTGCACCAGCT
GCACTGGCTTCCCCCTCAGCACCAGGGTACCAGGAGCTGAGGAGTGTGAG
CGTGCCGTCATCGACTTTGTGGCTTTCCAGGACATCTCCAT

FIG. 3

| | | |
|---|---|---|
| SEQ ID NO:4 | 128 | GCCGAGACAGCCCCACGACGTGTGGCCCGTGTCCACCGCGCCACTACACG |
| SEQ ID NO:5 | 1 | GCCGAGACAGCCCCACGACGTGTGGCCCGTGTCCACCGCGCNACTACACG |
| SEQ ID NO:6 | 1 | G |
| SEQ ID NO:3 | 1 | GCCGAGACAGCCCCACGACGTGTGGCCCGTGTCCACCGCGCCACTACACG |
| | | |
| SEQ ID NO:4 | 178 | CA-TTCTGGAACTACCTGGAGCGC |
| SEQ ID NO:5 | 51 | CAGTTCTGGAANTAACTGGAGCNCTGCCGCTACTGNAACGTCCTCTGNGG |
| SEQ ID NO:6 | 2 | CAGTTCTGGAACTACCTGGAGCGCTGCCGCTACTGCAACGTCCTCTGCGG |
| SEQ ID NO:3 | 51 | CAGTTCTGGAANTAACTGGAGCNCTGCCGCTACTGNAACGTCCTCTGNGG |
| | | |
| SEQ ID NO:5 | 101 | GGAGCNTGAGGAGGAGGCANGNGCTTGCCACGCCACCCACAACCGCGCCT |
| SEQ ID NO:6 | 52 | GGAGCGTGAGGAGGAGGCACGGGCTTGCCACGCCACCCACAACCGTGCCT |
| SEQ ID NO:7 | 1 | GAGGGGCCCCAGGAGTGGTGGCCGGAGGTG |
| SEQ ID NO:3 | 101 | GGAGCGTGAGGAGGAGGCACGGGCTTGCCACGCCACCCACAACCGTGCCT |
| | | |
| SEQ ID NO:5 | 151 | GCNGCTGCAGCACCGGNTTCTTCGCGCACGCTGNTTTCTGCTTGGAGCAC |
| SEQ ID NO:6 | 102 | GCCGCTGCCGCACCGGCTTCTTCGCGCACGCTGGTTTCTGCTTGGAGCAC |
| SEQ ID NO:7 | 32 | TGGCAGGGGTCAGGTTGCTGGTCCCAGCCTTGCACCCTGAGCTAGGACAC |
| SEQ ID NO:3 | 151 | GCCGCTGCCGCACCGGCTTCTTCGCGCACGCTGGTTTCTGCTTGGAGCAC |
| | | |
| SEQ ID NO:5 | 201 | GCATCGTGTCCACCTGGTGNCGGCGTGATTGCNCCGGGCACCCCAGCCA |
| SEQ ID NO:6 | 152 | GCATCGTGTCCACCTGGTGCCGGCGTGATTNCCCCGGGCACCCCAGCCA |
| SEQ ID NO:7 | 82 | CAGTTCCCCTGACCCTGTTCTTCCCTCCTGGCTGCAGGCACCCCAGCCA |
| SEQ ID NO:8 | 1 | GCATCGTGTCCACCTGGTGCCGGCGTGATTGCCCCGGGCACCCCAGCCA |
| SEQ ID NO:10 | 1 | CTTGTCCACCTGGTGCCGGCGTGATTNCCC-GGGCACCCCAGCCA |
| SEQ ID NO:3 | 201 | GCATCGTGTCCACCTGGTGCCGGCGTGATTGCCCCGGGCACCCCAGCCA |
| | | |
| SEQ ID NO:5 | 251 | GAACACGCA-TGCAAAGCCGTG |
| SEQ ID NO:7 | 132 | GAACACGCAGN-CC-AGCCGTGCCCCCCAGGCACCTTCTCAGCCAGCAGC |
| SEQ ID NO:8 | 51 | GAACACGCAG-GCCTAGCCGTGCCCCCCAGGCACCTTCTCAGCCAGCAGC |
| SEQ ID NO:10 | 47 | GAACACGCAGTGCC-AGCCNT-CCCCCCAGGCACCTTCTCAGCCAGCAGC |
| SEQ ID NO:9 | 1 | AGCNGTGCNCCNCAGGCACCTTCTCAGCCAGCAGT |
| SEQ ID NO:3 | 251 | GAACACGCAGTGCCTAGCCGTGCCCCCCAGGCACCTTCTCAGCCAGCAGC |
| | | |
| SEQ ID NO:7 | 182 | TCCAGCTCAGAGCAGTGCCAGCCCCACCGCAACTGCACGGCCCTGGGCCT |
| SEQ ID NO:8 | 101 | TCCAGCTCAGAGCAGTGCCAGCCCCACCGCAACTGCACGGCCCTGGGCCT |
| SEQ ID NO:10 | 97 | TCCAGCTCAGAGCAGTGCCAGCCCCACCGCAACTGCAACGCCCTGGNC-T |
| SEQ ID NO:9 | 36 | TCCAGCTCAGAGCAGTGCCAGCCCCACGGCAACTGCACGGCCCTGGGCCT |
| SEQ ID NO:3 | 301 | TCCAGCTCAGAGCAGTGCCAGCCCCACCGCAACTGCACGGCCCTGGGCCT |
| | | |
| SEQ ID NO:7 | 232 | GGCCCTCAATGTGCCAGGCTCTTCCTCCCATGACACCCTGTGCACCAG |
| SEQ ID NO:8 | 151 | GGCCCTCAATGTGCCAGGCTCTTCCTCCCATGACACCCTGTGCACCAGCT |
| SEQ ID NO:10 | 147 | GGCCCTCAATGTGCCAGGCTCTTCCTCCCATGACACCCTGTGCACCAGCT |
| SEQ ID NO:9 | 86 | GGCCCTCAATGTGCCAGGCTCTTCCTCCCATGACACGCTGTGCACCAGCT |
| SEQ ID NO:3 | 351 | GGCCCTCAATGTGCCAGGCTCTTCCTCCCATGACACCCTGTGCACCAGCT |
| | | |
| SEQ ID NO:10 | 197 | GCACTGGCTTCCCCCTCAGCACCAGGGTACCAGGAGCTGAGGAGTGTGAG |
| SEQ ID NO:9 | 136 | GCACTGGCTTCCCCCTCAGCACCAGGGTANCAGGAGCTGAGGAGTGTGAG |
| SEQ ID NO:3 | 401 | GCACTGGCTTCCCCCTCAGCACCAGGGTACCAGGAGCTGAGGAGTGTGAG |
| | | |
| SEQ ID NO:10 | 247 | CGTGCCGTCATCGACTTTGTGGCTTTCCAGGACATCTCCAT |
| SEQ ID NO:9 | 186 | CGTGCCGTCATCGACTTTGTGGCTTTCCAGGACATCTCCAT |
| SEQ ID NO:3 | 451 | CGTGCCGTCATCGACTTTGTGGCTTTCCAGGACATCTCCAT |

FIG. 4

```
DNA30942    1
hTNFR2      1    MAPVAVWAALAVGLELWAAAHALPAQVAFTPYPVRD.AETG

DNA30942   45    ERRLVCAQCPPGTFVQRPCRRDSPTTCGPCPPRHYTQFWNYLERCRYCNVL
hTNFR2     50    AQMCCSKCSPGQHAKVFCTKTSDTVCDSCEDSTYTQLWNWVPECLSCGSR

DNA30942   95    CGRRBEARACHATHREQNRICTCRRTGFF..AHAG..FCLEHASCPPGAGV
hTNFR2    100    CSSDQVETQACTREQNRICTCRPGWYCALSKQBGCRLCAPLRKCRPGFGV

DNA30942  139    IAPGTPPSQNTQCQPCPPGTPSASSGGEQCQPHRNCTALGLALNVPGSSS
hTNFR2    150    ARPGTETSDVVCKPCAPGTFSNTTSSTDICRPHQICNVVA....IPGNAS

DNA30942  189    HDTLCTSCTGFPLSTRVPGARECERAVIDFVAFQDISIKRLQRLLQALEA
hTNFR2    196    RDAVCTSTS..PTRSMAPGAVHLPQPVSTRSQHTQPTPEPSTAPSTSFLL

DNA30942  239    PEGWGPTP..RAGRAALQLKLRRRLTELGAQDGALLVRLLQALRVARMP.
hTNFR2    244    PMGPSPPAEGSTGDFALPVGLIVGVTALGLLIIGVVNCVIMTQVKKKPL.

DNA30942  287    GLERSVRERFLPVH
hTNFR2    293    CLQREAKVPHLPADKARGTQGPEQQHLLITAPSSSSSLESSASAALDRRA hTNFR2    343    PTRNQPQAPGVEASGAGEARASTGSSDSSPGGHGTQVNVTCIVNVCSSSD hTNFR2    393    HSSQCSSQASSTMGDTDSSPSESPKDEQVPFSKEECAFRSQLETPETLLG hTNFR2    443    STEEKPLPLGVPDAGMKPS
```

```
DcR3    1   M R A     L  E G P G L S L  L L C  L  V L A L P A L L P V  P  A V R G V A   31
OPG     1   M  N  K L L  C C A L V F  L D  L  S I K W T T Q E T F P - - - - -           25

DcR3   32   B T  P  T Y P W N R  D  A  E T  G E R  L V  C  A Q  C  P P G T  P V Q R P  C   62
OPG    26   - -  P  K Y L H Y D  E  E  T  S H Q L  L  C  D K  C  P P G T Y L K Q H  C   54

DcR3   63   R R D S P T  T  C  G  P  C  P P R H Y T Q P  W  N Y L E R  C  R Y C N V   93
OPG    55   T A K W K  T V  C  A P  C  P D H Y Y T D S  W  H T S D E  C  L Y  C  S P   85
                                         CRD1

DcR3   94   L C  G  E R E E A R R  A  C H A T H N R  A C  R C R T G  F  P A H A G   124
OPG    86   V  C  K  E  L Q Y V K Q E  C N R T H N R V  C  E  C  K  E  G  R Y L E I R   116
                                         CRD2

DcR3  125   F C L  E H A S C P P G A  G V I A P G T P S Q N T  C  O P  C  P P   155
OPG   117   F C L  K H R S C P P G F  G V V Q A G T P E R N T V C  K  R  C  P D   147
                                         CRD3

DcR3  156   G T F B A S S S E Q  D C  Q P  H  R N C T A L G L A L N V P  G  S   186
OPG   148   G F F S N E T S S K A P  C  R K H T N C S V F G L L L T Q K  G N   178
                                         CRD4

DcR3  187   S S H D T L  C  T S C  T G F P L S T R V P G A B E C E R  A  V I D   217
OPG   179   A T H D N I  C  S G N S E S T Q K C G I D - V T L  C E E  A  F F R   208

DcR3  218   F V A F Q D I S I K R  L  Q R  L  O A L E A P E G W G P T  -  P  R   247
OPG   209   F A V P T X F T P N W L  S V  L V D N L P G T X V N A E S V E R   239

DcR3  248   A G R A A L Q L K L R R R  L T  E L L G A Q D G  A  L - L  V  R L L   277
OPG   240   I K R Q H S S Q E Q T F Q L L  K L W K H Q  N  K A Q D I  V  K K I   270

DcR3  278   Q A L R V A R M P G L E R  S V R E R F  L  P V H 300
OPG   271   I O D I D L C E N S V Q R  H I G H A N L  T  F E 293...
```

| mAb | Isotype | Antigen Specificity (ELISA) | | | | | | % Blocking (ELISA) |
|---|---|---|---|---|---|---|---|---|
| | | DcR3 | DR4 | DR5 | DcR1 | OPG | | |
| 4B7.1.1 | IgG1 | +++ | - | - | - | - | | + |
| 4C4.1.4 | IgG2a | +++ | - | - | - | - | | - |
| 5C4.14.7 | IgG2b | +++ | - | - | - | - | | ++ |
| 8D3.1.5 | IgG1 | +++ | - | - | - | - | | +/- |
| 11C5.2.8 | IgG1 | +++ | - | - | - | - | | ++ |

Antigen specificity was determined using 10 microgram/ml mAb.
% blocking activity was determined by ELISA at 100 fold excess of mAb to Fas ligand.

FIG. 12

SEQUENCE LISTING

<160> NUMBER OF SEQ ID NOS: 18

<210> SEQ ID NO 1
<211> LENGTH: 300
<212> TYPE: PRT
<213> ORGANISM: Homo sapiens

<400> SEQUENCE: 1

Met Arg Ala Leu Glu Gly Pro Gly Leu Ser Leu Leu Cys Leu Val
 1               5                  10                  15

Leu Ala Leu Pro Ala Leu Leu Pro Val Pro Ala Val Arg Gly Val
                20                  25                  30

Ala Glu Thr Pro Thr Tyr Pro Trp Arg Asp Ala Glu Thr Gly Glu

-continued

```
                35                  40                  45
Arg Leu Val Cys Ala Gln Cys Pro Pro Gly Thr Phe Val Gln Arg
         50                  55                  60
Pro Cys Arg Arg Asp Ser Pro Thr Thr Cys Gly Pro Cys Pro Pro
         65                  70                  75
Arg His Tyr Thr Gln Phe Trp Asn Tyr Leu Glu Arg Cys Arg Tyr
         80                  85                  90
Cys Asn Val Leu Cys Gly Glu Arg Glu Glu Ala Arg Ala Cys
         95                 100                 105
His Ala Thr His Asn Arg Ala Cys Arg Cys Arg Thr Gly Phe Phe
        110                 115                 120
Ala His Ala Gly Phe Cys Leu Glu His Ala Ser Cys Pro Pro Gly
        125                 130                 135
Ala Gly Val Ile Ala Pro Gly Thr Pro Ser Gln Asn Thr Gln Cys
        140                 145                 150
Gln Pro Cys Pro Pro Gly Thr Phe Ser Ala Ser Ser Ser Ser
        155                 160                 165
Glu Gln Cys Gln Pro His Arg Asn Cys Thr Ala Leu Gly Leu Ala
        170                 175                 180
Leu Asn Val Pro Gly Ser Ser His Asp Thr Leu Cys Thr Ser
        185                 190                 195
Cys Thr Gly Phe Pro Leu Ser Thr Arg Val Pro Gly Ala Glu Glu
        200                 205                 210
Cys Glu Arg Ala Val Ile Asp Phe Val Ala Phe Gln Asp Ile Ser
        215                 220                 225
Ile Lys Arg Leu Gln Arg Leu Leu Gln Ala Leu Glu Ala Pro Glu
        230                 235                 240
Gly Trp Gly Pro Thr Pro Arg Ala Gly Arg Ala Ala Leu Gln Leu
        245                 250                 255
Lys Leu Arg Arg Arg Leu Thr Glu Leu Leu Gly Ala Gln Asp Gly
        260                 265                 270
Ala Leu Leu Val Arg Leu Leu Gln Ala Leu Arg Val Ala Arg Met
        275                 280                 285
Pro Gly Leu Glu Arg Ser Val Arg Glu Arg Phe Leu Pro Val His
        290                 295                 300
```

<210> SEQ ID NO 2
<211> LENGTH: 1114
<212> TYPE: DNA
<213> ORGANISM: Homo sapiens
<220> FEATURE:
<221> NAME/KEY: Unsure
<222> LOCATION: 1090
<223> OTHER INFORMATION: Unknown base

<400> SEQUENCE: 2

| | | |
|---|---|---|
| tccgcaggcg gaccgggggc aaaggaggtg gcatgtcggt caggcacagc | | 50 |
| agggtcctgt gtccgcgctg agccgcgctc tccctgctcc agcaaggacc | | 100 |
| atgagggcgc tggagggggcc aggcctgtcg ctgctgtgcc tggtgttggc | | 150 |
| gctgcctgcc ctgctgccgg tgccggctgt acgcggagtg gcagaaacac | | 200 |
| ccacctaccc ctggcgggac gcagagacag gggagcggct ggtgtgcgcc | | 250 |
| cagtgccccc caggcacctt tgtgcagcgg ccgtgccgcc gagacagccc | | 300 |
| cacgacgtgt ggcccgtgtc caccgcgcca ctacacgcag ttctggaact | | 350 |

```
acctggagcg ctgccgctac tgcaacgtcc tctgcgggga gcgtgaggag        400
gaggcacggg cttgccacgc cacccacaac cgtgcctgcc gctgccgcac        450
cggcttcttc gcgcacgctg gtttctgctt ggagcacgca tcgtgtccac        500
ctggtgccgg cgtgattgcc ccgggcaccc ccagccagaa cacgcagtgc        550
cagccgtgcc ccccaggcac cttctcagcc agcagctcca gctcagagca        600
gtgccagccc caccgcaact gcacggccct gggcctggcc ctcaatgtgc        650
caggctcttc ctcccatgac accctgtgca ccagctgcac tggcttcccc        700
ctcagcacca gggtaccagg agctgaggag tgtgagcgtg ccgtcatcga        750
ctttgtggct ttccaggaca tctccatcaa gaggctgcag cggctgctgc        800
aggccctcga ggccccggag ggctggggtc gacaccaag gcggcccgc         850 gcggccttgc agctgaagct gcgtcggcgg ctcacggagc tcctgggggc        900
gcaggacggg gcgctgctgg tgcggctgct gcaggcgctg cgcgtggcca        950
ggatgcccgg gctggagcgg agcgtccgtg agcgcttcct ccctgtgcac        1000
tgatcctggc cccctcttat ttattctaca tccttggcac cccacttgca        1050
ctgaaagagg cttttttta aatagaagaa atgaggtttn ttaaaaaaaa         1100 aaaaaaaaa aaaa 1114

<210> SEQ ID NO 3
<211> LENGTH: 491
<212> TYPE: DNA
<213> ORGANISM: Unknown
<220> FEATURE:
<223> OTHER INFORMATION: Unknown organism
<221> NAME/KEY: unsure
<222> LOCATION: 62, 73, 86, 98
<223> OTHER INFORMATION: unknown base

<400> SEQUENCE: 3
gccgagacag ccccacgacg tgtggcccgt gtccaccgcg ccactacacg         50
cagttctgga antaactgga gcnctgccgc tactgnaacg tcctctgngg        100
ggagcgtgag gaggaggcac gggcttgcca cgccacccac aaccgtgcct        150
gccgctgccg caccggcttc ttcgcgcacg ctggtttctg cttggagcac        200
gcatcgtgtc cacctggtgc cggcgtgatt gccccgggca ccccagcca         250 gaacacgcag tgcctagccg tgccccccag gcacttctc agccagcagc         300 tccagctcag agcagtgcca gccccaccgc aactgcacgg ccctgggcct        350
ggccctcaat gtgccaggct cttcctccca tgacaccctg tgcaccagct        400
gcactggctt cccctcagc accagggtac caggagctga ggagtgtgag         450
cgtgccgtca tcgactttgt ggctttccag gacatctcca t                491

<210> SEQ ID NO 4
<211> LENGTH: 73
<212> TYPE: DNA
<213> ORGANISM: Unknown
<220> FEATURE:
<223> OTHER INFORMATION: Unknown organism

<400> SEQUENCE: 4
gccgagacag ccccacgacg tgtggcccgt gtccaccgcg ccactacacg          50
cattctggaa ctacctggag cgc                                      73
```

-continued

<210> SEQ ID NO 5
<211> LENGTH: 271
<212> TYPE: DNA
<213> ORGANISM: Unknown
<220> FEATURE:
<223> OTHER INFORMATION: Unknown organism
<221> NAME/KEY: unsure
<222> LOCATION: 42, 62, 73, 86, 98, 106, 120, 122, 153, 167, 184, 220,
      233
<223> OTHER INFORMATION: unknown base

<400> SEQUENCE: 5
gccgagacag ccccacgacg tgtggcccgt gtccaccgcg cnactacacg            50
cagttctgga antaactgga gcnctgccgc tactgnaacg tcctctgngg           100
ggagcntgag gaggaggcan gngcttgcca cgccacccac aaccgcgcct           150
gcngctgcag caccggnttc ttcgcgcacg ctgntttctg cttggagcac           200
gcatcgtgtc cacctggtgn cggcgtgatt gcnccgggca cccccagcca           250
gaacacgcat gcaaagccgt g                                          271

<210> SEQ ID NO 6
<211> LENGTH: 201
<212> TYPE: DNA
<213> ORGANISM: Unknown
<220> FEATURE:
<223> OTHER INFORMATION: Unknown organism
<221> NAME/KEY: unsure
<222> LOCATION: 182
<223> OTHER INFORMATION: unknown base

<400> SEQUENCE: 6
gcagttctgg aactacctgg agcgctgccg ctactgcaac gtcctctgcg            50
gggagcgtga ggaggaggca cgggcttgcc acgccaccca caaccgtgcc           100
tgccgctgcc gcaccggctt cttcgcgcac gctggtttct gcttggagca           150
cgcatcgtgt ccacctggtg ccggcgtgat tnccccgggc accccagcc            200 a                                                                201

<210> SEQ ID NO 7
<211> LENGTH: 277
<212> TYPE: DNA
<213> ORGANISM: Unknown
<220> FEATURE:
<223> OTHER INFORMATION: Unknown organism
<221> NAME/KEY: unsure
<222> LOCATION: 142
<223> OTHER INFORMATION: unknown base

<400> SEQUENCE: 7
gaggggcccc caggagtggt ggccggaggt gtggcagggg tcaggttgct            50
ggtcccagcc ttgcaccctg agctaggaca ccagttcccc tgaccctgtt           100
cttccctcct ggctgcaggc accccagcc agaacacgca gnccagccgt            150 gcccccagg caccttctca gccagcagct ccagctcaga gcagtgccag            200
ccccaccgca actgcacggc cctgggcctg gccctcaatg tgccaggctc           250
ttcctcccat gacaccctgt gcaccag                                    277

<210> SEQ ID NO 8
<211> LENGTH: 199
<212> TYPE: DNA
<213> ORGANISM: Unknown

```
<220> FEATURE:
<223> OTHER INFORMATION: Unknown organism

<400> SEQUENCE: 8
gcatcgtgtc cacctggtgc cggcgtgatt gccccgggca cccccagcca        50
gaacacgcag gcctagccgt gccccccagg caccttctca gccagcagct       100
ccagctcaga gcagtgccag ccccaccgca actgcacggc cctgggcctg       150
gccctcaatg tgccaggctc ttcctcccat gacaccctgt gcaccagct        199

<210> SEQ ID NO 9
<211> LENGTH: 226
<212> TYPE: DNA
<213> ORGANISM: Unknown
<220> FEATURE:
<223> OTHER INFORMATION: Unknown organism
<221> NAME/KEY: unsure
<222> LOCATION: 4, 9, 12, 165
<223> OTHER INFORMATION: unknown base

<400> SEQUENCE: 9
agcngtgcnc ncaggcacc ttctcagcca gcagttccag ctcagagcag        50
tgccagcccc accgcaactg cacggccctg ggcctggccc tcaatgtgcc       100
aggctcttcc tcccatgaca cgctgtgcac cagctgcact ggcttccccc       150
tcagcaccag ggtancagga gctgaggagt gtgagcgtgc cgtcatcgac       200
tttgtggctt ccaggacat ctccat                                  226

<210> SEQ ID NO 10
<211> LENGTH: 283
<212> TYPE: DNA
<213> ORGANISM: Homo sapiens
<220> FEATURE:
<221> NAME/KEY: Unsure
<222> LOCATION: 1-283
<223> OTHER INFORMATION: Unknown organism
<221> NAME/KEY: unsure
<222> LOCATION: 27, 64, 140
<223> OTHER INFORMATION: unknown base

<400> SEQUENCE: 10
cttgtccacc tggtgccggc gtgattnccc gggcacccccc agccagaaca       50 cgcagtgcca gccntccccc caggcacctt ctcagccagc agctccagct      100
cagagcagtg ccagccccac cgcaactgca acgccctggn ctggccctca      150
atgtgccagg ctcttcctcc catgacaccc tgtgcaccag ctgcactggc      200
ttccccctca gcaccaggt accaggagct gaggagtgtg agcgtgccgt        250
catcgacttt gtggctttcc aggacatctc cat                         283

<210> SEQ ID NO 11
<211> LENGTH: 21
<212> TYPE: DNA
<213> ORGANISM: Unknown
<220> FEATURE:
<223> OTHER INFORMATION: Unknown organism

<400> SEQUENCE: 11
cacgctggtt tctgcttgga g                                      21

<210> SEQ ID NO 12
<211> LENGTH: 22
<212> TYPE: DNA
```

```
<213> ORGANISM: Unknown
<220> FEATURE:
<223> OTHER INFORMATION: Unknown organism

<400> SEQUENCE: 12
agctggtgca cagggtgtca tg                                              22

<210> SEQ ID NO 13
<211> LENGTH: 53
<212> TYPE: DNA
<213> ORGANISM: Unknown
<220> FEATURE:
<223> OTHER INFORMATION: Unknown organism

<400> SEQUENCE: 13
cccaggcacc ttctcagcca gccagcagct ccagctcaga gcagtgccag                50
ccc                                                                   53

<210> SEQ ID NO 14
<211> LENGTH: 24
<212> TYPE: DNA
<213> ORGANISM: Unknown
<220> FEATURE:
<223> OTHER INFORMATION: Unknown organism

<400> SEQUENCE: 14
acacgatgcg tgctccaagc agaa                                            24

<210> SEQ ID NO 15
<211> LENGTH: 17
<212> TYPE: DNA
<213> ORGANISM: Unknown
<220> FEATURE:
<223> OTHER INFORMATION: Unknown organism

<400> SEQUENCE: 15
cttcttcgcg cacgctg                                                    17

<210> SEQ ID NO 16
<211> LENGTH: 16
<212> TYPE: DNA
<213> ORGANISM: Unknown
<220> FEATURE:
<223> OTHER INFORMATION: Unknown organism

<400> SEQUENCE: 16
atcacgccgg caccag                                                     16

<210> SEQ ID NO 17
<211> LENGTH: 461
<212> TYPE: PRT
<213> ORGANISM: Homo sapiens

<400> SEQUENCE: 17
```

```
Met Ala Pro Val Ala Val Trp Ala Ala Leu Ala Val Gly Leu Glu
  1               5                  10                  15

Leu Trp Ala Ala Ala His Ala Leu Pro Ala Gln Val Ala Phe Thr
                 20                  25                  30

Pro Tyr Ala Pro Glu Pro Gly Ser Thr Cys Arg Leu Arg Glu Tyr
                 35                  40                  45

Tyr Asp Gln Thr Ala Gln Met Cys Cys Ser Lys Cys Ser Pro Gly
                 50                  55                  60

Gln His Ala Lys Val Phe Cys Thr Lys Thr Ser Asp Thr Val Cys
```

-continued

```
                65                  70                  75
Asp Ser Cys Glu Asp Ser Thr Tyr Thr Gln Leu Trp Asn Trp Val
                80                  85                  90
Pro Glu Cys Leu Ser Cys Gly Ser Arg Cys Ser Ser Asp Gln Val
                95                  100                 105
Glu Thr Gln Ala Cys Thr Arg Glu Gln Asn Arg Ile Cys Thr Cys
                110                 115                 120
Arg Pro Gly Trp Tyr Cys Ala Leu Ser Lys Gln Glu Gly Cys Arg
                125                 130                 135
Leu Cys Ala Pro Leu Arg Lys Cys Arg Pro Gly Phe Gly Val Ala
                140                 145                 150
Arg Pro Gly Thr Glu Thr Ser Asp Val Val Cys Lys Pro Cys Ala
                155                 160                 165
Pro Gly Thr Phe Ser Asn Thr Thr Ser Ser Thr Asp Ile Cys Arg
                170                 175                 180
Pro His Gln Ile Cys Asn Val Val Ala Ile Pro Gly Asn Ala Ser
                185                 190                 195
Arg Asp Ala Val Cys Thr Ser Thr Ser Pro Thr Arg Ser Met Ala
                200                 205                 210
Pro Gly Ala Val His Leu Pro Gln Pro Val Ser Thr Arg Ser Gln
                215                 220                 225
His Thr Gln Pro Thr Pro Glu Pro Ser Thr Ala Pro Ser Thr Ser
                230                 235                 240
Phe Leu Leu Pro Met Gly Pro Ser Pro Ala Glu Gly Ser Thr
                245                 250                 255
Gly Asp Phe Ala Leu Pro Val Gly Leu Ile Val Gly Val Thr Ala
                260                 265                 270
Leu Gly Leu Leu Ile Ile Gly Val Val Asn Cys Val Ile Met Thr
                275                 280                 285
Gln Val Lys Lys Lys Pro Leu Cys Leu Gln Arg Glu Ala Lys Val
                290                 295                 300
Pro His Leu Pro Ala Asp Lys Ala Arg Gly Thr Gln Gly Pro Glu
                305                 310                 315
Gln Gln His Leu Leu Ile Thr Ala Pro Ser Ser Ser Ser Ser
                320                 325                 330
Leu Glu Ser Ser Ala Ser Ala Leu Asp Arg Arg Ala Pro Thr Arg
                335                 340                 345
Asn Gln Pro Gln Ala Pro Gly Val Glu Ala Ser Gly Ala Gly Glu
                350                 355                 360
Ala Arg Ala Ser Thr Gly Ser Ser Asp Ser Ser Pro Gly Gly His
                365                 370                 375
Gly Thr Gln Val Asn Val Thr Cys Ile Val Asn Val Cys Ser Ser
                380                 385                 390
Ser Asp His Ser Ser Gln Cys Ser Ser Gln Ala Ser Ser Thr Met
                395                 400                 405
Gly Asp Thr Asp Ser Ser Pro Ser Glu Ser Pro Lys Asp Glu Gln
                410                 415                 420
Val Pro Phe Ser Lys Glu Glu Cys Ala Phe Arg Ser Gln Leu Glu
                425                 430                 435
Thr Pro Glu Thr Leu Leu Gly Ser Thr Glu Glu Lys Pro Leu Pro
                440                 445                 450
```

```
Leu Gly Val Pro Asp Ala Gly Met Lys Pro Ser
            455                 460

<210> SEQ ID NO 18
<211> LENGTH: 293
<212> TYPE: PRT
<213> ORGANISM: Homo sapiens

<400> SEQUENCE: 18

Met Asn Lys Leu Leu Cys Cys Ala Leu Val Phe Leu Asp Ile Ser
  1               5                  10                  15

Ile Lys Trp Thr Thr Gln Glu Thr Phe Pro Pro Lys Tyr Leu His
                 20                  25                  30

Tyr Asp Glu Glu Thr Ser His Gln Leu Leu Cys Asp Lys Cys Pro
                 35                  40                  45

Pro Gly Thr Tyr Leu Lys Gln His Cys Thr Ala Lys Trp Lys Thr
                 50                  55                  60

Val Cys Ala Pro Cys Pro Asp His Tyr Tyr Thr Asp Ser Trp His
                 65                  70                  75

Thr Ser Asp Glu Cys Leu Tyr Cys Ser Pro Val Cys Lys Glu Leu
                 80                  85                  90

Gln Tyr Val Lys Gln Glu Cys Asn Arg Thr His Asn Arg Val Cys
                 95                 100                 105

Glu Cys Lys Glu Gly Arg Tyr Leu Glu Ile Glu Phe Cys Leu Lys
                110                 115                 120

His Arg Ser Cys Pro Pro Gly Phe Gly Val Val Gln Ala Gly Thr
                125                 130                 135

Pro Glu Arg Asn Thr Val Cys Lys Arg Cys Pro Asp Gly Phe Phe
                140                 145                 150

Ser Asn Glu Thr Ser Ser Lys Ala Pro Cys Arg Lys His Thr Asn
                155                 160                 165

Cys Ser Val Phe Gly Leu Leu Leu Thr Gln Lys Gly Asn Ala Thr
                170                 175                 180

His Asp Asn Ile Cys Ser Gly Asn Ser Glu Ser Thr Gln Lys Cys
                185                 190                 195

Gly Ile Asp Val Thr Leu Cys Glu Glu Ala Phe Phe Arg Phe Ala
                200                 205                 210

Val Pro Thr Lys Phe Thr Pro Asn Trp Leu Ser Val Leu Val Asp
                215                 220                 225

Asn Leu Pro Gly Thr Lys Val Asn Ala Glu Ser Val Glu Arg Ile
                230                 235                 240

Lys Arg Gln His Ser Ser Gln Glu Gln Thr Phe Gln Leu Leu Lys
                245                 250                 255

Leu Trp Lys His Gln Asn Lys Ala Gln Asp Ile Val Lys Lys Ile
                260                 265                 270

Ile Gln Asp Ile Asp Leu Cys Glu Asn Ser Val Gln Arg His Ile
                275                 280                 285

Gly His Ala Asn Leu Thr Phe Glu
                290
```

ANTIBODIES TO DCR3 POLYPEPTIDE, A TNFR HOMOLOG

RELATED APPLICATIONS

This application is a continuation application of Ser. No. 09/157,289 filed Sep. 18, 1998, now abandoned, which is a non-provisional application claiming priority under Section 119(e) to provisional application No. 60/059,288 filed Sep. 18, 1997 and to provisional application No. 60/094,640 filed Jul. 30, 1998, the contents of which are hereby incorporated by reference.

FIELD OF THE INVENTION

The present invention relates generally to the identification and isolation of novel DNA and to the recombinant production of novel polypeptides, designated herein as "DcR3".

BACKGROUND OF THE INVENTION

Various molecules, such as tumor necrosis factor-α ("TNF-α"), tumor necrosis factor-β ("TNF-β" or "lymphotoxin"), CD30 ligand, CD27 ligand, CD40 ligand, OX-40 ligand, 4-1BB ligand, Fas ligand (also referred to as Apo-1 ligand or CD95 ligand), and Apo-2 ligand (also referred to as TRAIL) have been identified as members of the tumor necrosis factor ("TNF") family of cytokines [See, e.g., Gruss and Dower, Blood, 85:3378–3404 (1995); Wiley et al., Immunity, 3:673–682 (1995); Pitti et al., J. Biol. Chem., 271:12687–12690 (1996)]. Among these molecules, TNF-α, TNF-β, CD30 ligand, 4-1BB ligand, Fas ligand, and Apo-2 ligand (TRAIL) have been reported to be involved in apoptotic cell death. Both TNF-α and TNF-β have been reported to induce apoptotic death in susceptible tumor cells [Schmid et al., Proc. Natl. Acad. Sci., 83:1881 (1986); Dealtry et al., Eur. J. Immunol., 17:689 (1987)]. Zheng et al. have reported that TNF-α is involved in post-stimulation apoptosis of CD8-positive T cells [Zheng et al., Nature, 377:348–351 (1995)]. Other investigators have reported that CD30 ligand may be involved in deletion of self-reactive T cells in the thymus [Amakawa et al., Cold Spring Harbor Laboratory Symposium on Programmed Cell Death, Abstr. No. 10, (1995)].

Fas ligand appears to regulate primarily three types of apoptosis: (a) activation-induced cell death (AICD) of mature T lymphocytes; (b) elimination of inflammatory cells from immune-privileged sites; and (c) killing of damaged cells by cytotoxic lymphocytes [Nagata, Cell, 88:355 (1997)]. It has been reported that T cell AICD assists in shutting down the host's immune response once an infection has been cleared. Repeated stimulation of the T cell receptor (TCR) by antigen induced expression of Fas ligand and Fas on the surface of T helper cells; subsequently Fas ligand engages Fas and can trigger apoptosis in the activated lymphocytes, leading to their elimination. Immune-privileged sites include tissues such as the eye, brain or testis, in which inflammatory immune responses can perturb function. Cells in immune privileged sites appear to constitutively express Fas ligand, and eliminate infiltrating leukocytes that express Fas through Fas dependent apoptosis. Certain cancers including melanomas [Hahne et al., Science, 274:1363 (1996)] and hepatocellular carcinomas [Strand et al., Nature Med., 2:1361–1366 (1996)] use a similar Fas ligand-dependent mechanism to evade immune surveillance. Natural killer (NK) cells and cytotoxic T lymphocytes have been reported to eliminate cells that have been damaged by viral or bacterial infection or by oncogenic transformation by at least two pathways. One pathway involves release of perforin and granzymes, and an alternative pathway involves expression of Fas ligand and induction of apoptosis by engagement of Fas on target cells [Nagata, supra; Moretta, Cell, 90:13 (1997)].

Mutations in the mouse Fas/Apo-1 receptor or ligand genes (called 1pr and gld, respectively) have been associated with some autoimmune disorders, indicating that Fas ligand may play a role in regulating the clonal deletion of self-reactive lymphocytes in the periphery [Krammer et al., Curr. Op. Immunol., 6:279–289 (1994); Nagata et al., Science, 267:1449–1456 (1995)]. Fas ligand is also reported to induce post-stimulation apoptosis in CD4-positive T lymphocytes and in B lymphocytes, and may be involved in the elimination of activated lymphocytes when their function is no longer needed [Krammer et al., supra; Nagata et al., supra]. Agonist mouse monoclonal antibodies specifically binding to the Fas receptor have been reported to exhibit cell killing activity that is comparable to or similar to that of TNF-α [Yonehara et al., J. Exp. Med., 169:1747–1756 (1989)].

Induction of various cellular responses mediated by such TNF family cytokines is believed to be initiated by their binding to specific cell receptors. Two distinct TNF receptors of approximately 55-kDa (TNFR1) and 75-kDa (TNFR2) have been identified [Hohmann et al., J. Biol. Chem., 264:14927–14934 (1989); Brockhaus et al., Proc. Natl. Acad. Sci., 87:3127–3131 (1990); EP 417,563, published Mar. 20, 1991] and human and mouse cDNAs corresponding to both receptor types have been isolated and characterized [Loetscher et al., Cell, 61:351 (1990); Schall et al., Cell, 61:361 (1990); Smith et al., Science, 248:1019–1023 (1990); Lewis et al., Proc. Natl. Acad. Sci., 88:2830–2834 (1991); Goodwin et al., Mol. Cell. Biol., 11:3020–3026 (1991)]. Extensive polymorphisms have been associated with both TNF receptor genes [see, e.g., Takao et al., Immunogenetics, 37:199–203 (1993)]. Both TNFRs share the typical structure of cell surface receptors including extracellular, transmembrane and intracellular regions. The extracellular portions of both receptors are found naturally also as soluble TNF-binding proteins [Nophar, Y. et al., EMBO J., 9:3269 (1990); and Kohno, T. et al., Proc. Natl. Acad. Sci. U.S.A., 87:8331 (1990)]. More recently, the cloning of recombinant soluble TNF receptors was reported by Hale et al. [J. Cell. Biochem. Supplement 15F, 1991, p. 113 (P424)].

The extracellular portion of type 1 and type 2 TNFRs (TNFR1 and TNFR2) contains a repetitive amino acid sequence pattern of four cysteine-rich domains (CRDs) designated 1 through 4, starting from the $NH_2$-terminus. Each CRD is about 40 amino acids long and contains 4 to 6 cysteine residues at positions which are well conserved [Schall et al., supra; Loetscher et al., supra; Smith et al., supra; Nophar et al., supra; Kohno et al., supra]. In TNFR1, the approximate boundaries of the four CRDs are as follows: CRD1-amino acids 14 to about 53; CRD2-amino acids from about 54 to about 97; CRD3-amino acids from about 98 to about 138; CRD4-amino acids from about 139 to about 167. In TNFR2, CRD1 includes amino acids 17 to about 54; CRD2-amino acids from about 55 to about 97; CRD3-amino acids from about 98 to about 140; and CRD4-amino acids from about 141 to about 179 [Banner et al., Cell, 73:431–445 (1993)]. The potential role of the CRDs in ligand binding is also described by Banner et al., supra.

A similar repetitive pattern of CRDs exists in several other cell-surface proteins, including the p75 nerve growth factor receptor (NGFR) [Johnson et al., Cell, 47:545 (1986);

Radeke et al., *Nature*, 325:593 (1987)], the B cell antigen CD40 [Stamenkovic et al., *EMBO J.*, 8:1403 (1989)], the T cell antigen OX40 [Mallett et al., *EMBO J.*, 9:1063 (1990)] and the Fas antigen [Yonehara et al., supra and Itoh et al., *Cell*, 66:233–243 (1991)]. CRDs are also found in the soluble TNFR (sTNFR)-like T2 proteins of the Shope and myxoma poxviruses [Upton et al., *Virology*, 160:20–29 (1987); Smith et al., *Biochem. Biophys. Res. Commun.*, 176:335 (1991); Upton et al., *Virology*, 184:370 (1991)]. Optimal alignment of these sequences indicates that the positions of the cysteine residues are well conserved. These receptors are sometimes collectively referred to as members of the TNF/NGF receptor superfamily. Recent studies on p75NGFR showed that the deletion of CRD1 [Welcher, A. A. et al., *Proc. Natl. Acad. Sci. USA*, 88:159–163 (1991)] or a 5-amino acid insertion in this domain [Yan, H. and Chao, M. V., *J. Biol. Chem.*, 266:12099–12104 (1991)] had little or no effect on NGF binding [Yan, H. and Chao, M. V., supra]. p75 NGFR contains a proline-rich stretch of about 60 amino acids, between its CRD4 and transmembrane region, which is not involved in NGF binding [Peetre, C. et al., *Eur. J. Haematol.*, 41:414–419 (1988); Seckinger, P. et al., *J. Biol. Chem.*, 264:11966–11973 (1989); Yan, H. and Chao, M. V., supra]. A similar proline-rich region is found in TNFR2 but not in TNFR1.

Itoh et al. disclose that the Fas receptor can signal an apoptotic cell death similar to that signaled by the 55-kDa TNFR1 [Itoh et al., supra]. Expression of the Fas antigen has also been reported to be down-regulated along with that of TNFR1 when cells are treated with either TNF-α or anti-Fas mouse monoclonal antibody [Krammer et al., supra; Nagata et al., supra]. Accordingly, some investigators have hypothesized that cell lines that co-express both Fas and TNFR1 receptors may mediate cell killing through common signaling pathways [Id.].

The TNF family ligands identified to date, with the exception of lymphotoxin-α, are type II transmembrane proteins, whose C-terminus is extracellular. In contrast, most receptors in the TNF receptor (TNFR) family identified to date are type I transmembrane proteins. In both the TNF ligand and receptor families, however, homology identified between family members has been found mainly in the extracellular domain ("ECD"). Several of the TNF family cytokines, including TNF-α, Fas ligand and CD40 ligand, are cleaved proteolytically at the cell surface; the resulting protein in each case typically forms a homotrimeric molecule that functions as a soluble cytokine. TNF receptor family proteins are also usually cleaved proteolytically to release soluble receptor ECDs that can function as inhibitors of the cognate cytokines.

Recently, other members of the TNFR family have been identified. Such newly identified members of the TNFR family include CAR1, HVEM and osteoprotegerin (OPG) [Brojatsch et al., *Cell*, 87:845–855 (1996); Montgomery et al., *Cell*, 87:427–436 (1996); Marsters et al., *J. Biol. Chem.*, 272:14029–14032 (1997); Simonet et al., *Cell*, 89:309–319 (1997)]. Unlike other known TNFR-like molecules, Simonet et al., supra, report that OPG contains no hydrophobic transmembrane-spanning sequence.

In Marsters et al., *Curr. Biol.*, 6:750 (1996), investigators describe a full length native sequence human polypeptide, called Apo-3, which exhibits similarity to the TNFR family in its extracellular cysteine-rich repeats and resembles TNFR1 and CD95 in that it contains a cytoplasmic death domain sequence [see also Marsters et al., *Curr. Biol.*, 6:1669 (1996)]. Apo-3 has also been referred to by other investigators as DR3, wsl-1 and TRAMP [Chinnaiyan et al., *Science*, 274:990 (1996); Kitson et al., *Nature*, 384:372 (1996); Bodmer et al., *Immunity*, 6:79 (1997)].

Pan et al. have disclosed another TNF receptor family member referred to as "DR4" [Pan et al., *Science*, 276:111–113 (1997)]). The DR4 was reported to contain a cytoplasmic death domain capable of engaging the cell suicide apparatus. Pan et al. disclose that DR4 is believed to be a receptor for the ligand known as Apo-2 ligand or TRAIL.

In Sheridan et al., *Science*, 277:818–821 (1997) and Pan et al., *Science*, 277:815–818 (1997), another molecule believed to be a receptor for the Apo-2 ligand (TRAIL) is described. That molecule is referred to as DR5 (it has also been alternatively referred to as Apo-2). Like DR4, DR5 is reported to contain a cytoplasmic death domain and be capable of signaling apoptosis.

In Sheridan et al., supra, a receptor called DcR1 (or alternatively, Apo-2DcR) is disclosed as being a potential decoy receptor for Apo-2 ligand (TRAIL). Sheridan et al. report that DcR1 can inhibit Apo-2 ligand function in vitro. See also, Pan et al., supra, for disclosure on the decoy receptor referred to as TRID.

For a review of the TNF family of cytokines and their receptors, see Gruss and Dower, supra.

Membrane-bound proteins and receptors can play an important role in the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesin molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immunoadhesins, for instance, can be employed as therapeutic agents to block receptor-ligand interaction. The membrane-bound proteins can also be employed for screening of potential peptide or small molecule inhibitors of the relevant receptor/ligand interaction.

Efforts are being undertaken by both industry and academia to identify new, native receptor proteins. Many efforts are focused on the screening of mammalian recombinant DNA libraries to identify the coding sequences for novel receptor proteins.

SUMMARY OF THE INVENTION

Applicants have identified a cDNA clone that encodes a novel polypeptide, designated in the present application as "DcR3." The term "DcR3" as used herein refers to the same polypeptides previously referred to by Applicants as "DNA30942".

In one embodiment, the invention provides an isolated nucleic acid molecule comprising DNA encoding DcR3 polypeptide. In one aspect, the isolated nucleic acid comprises DNA encoding DcR3 polypeptide having amino acid residues 1 to 300 of FIG. 1 (SEQ ID NO:1); residues 1 to 215 of FIG. 1 (SEQ ID NO:1); or residues 1 to x, where x is any one of residues 215 to 300 of FIG. 1 (SEQ ID NO:1), or is complementary to such encoding nucleic acid sequence, and remains stably bound to it under at least moderate, and optionally, under high stringency conditions.

In another embodiment, the invention provides a vector comprising DNA encoding DcR3 polypeptide. A host cell comprising such a vector is also provided. By way of example, the host cells may be CHO cells, E. coli, or yeast. A process for producing DcR3 polypeptides is further provided and comprises culturing host cells under conditions suitable for expression of DcR3 and recovering DcR3 from the cell culture.

In another embodiment, the invention provides isolated DcR3 polypeptide. In particular, the invention provides isolated native sequence DcR3 polypeptide, which in one embodiment, includes an amino acid sequence comprising residues 1 to 300 of FIG. 1 (SEQ ID NO:1) or residues 1 to 215 of FIG. 1 (SEQ ID NO:1) or residues 1 to x, where x is any one of residues 215 to 300 of FIG. 1 (SEQ ID NO:1).

In another embodiment, the invention provides isolated DcR3 variants. The DcR3 variants comprise polypeptides which have at least about 80% amino acid sequence identity with the deduced amino acid sequence of FIG. 1 (SEQ ID NO:1) or domain sequences identified herein, and preferably have activity(s) of native or naturally-occurring DcR3.

In another embodiment, the invention provides chimeric molecules comprising DcR3 polypeptide fused to a heterologous polypeptide or amino acid sequence. An example of such a chimeric molecule comprises a DcR3 fused to an epitope tag sequence or a Fc region of an immunoglobulin.

In another embodiment, the invention provides an antibody which specifically binds to DcR3 polypeptide. Optionally, the antibody is a monoclonal antibody. Optionally, the antibody is a monoclonal antibody which specifically binds to DcR3 and blocks its binding to Fas ligand and/or other ligands recognized by DcR3.

In a further embodiment, the invention provides agonists and antagonists of DcR3 polypeptide. Therapeutic and diagnostic methods are also provided.

In another embodiment, the invention provides an expressed sequence tag (EST) comprising the nucleotide sequence of FIG. 3 (SEQ ID NO:3).

BRIEF DESCRIPTION OF THE DRAWINGS

FIG. 1 shows the derived amino acid sequence of a native sequence DcR3 (SEQ ID NO:1).

FIG. 2 shows the nucleotide sequence of a native sequence DcR3 cDNA (SEQ ID NO:2).

FIG. 3 shows an EST nucleotide sequence (SEQ ID NO:3).

FIG. 4 shows various ESTs (SEQ ID NOs: 3–10) used in the assembly of the consensus sequence.

FIG. 5 shows an alignment of DcR3 (SEQ ID NO:1) and human TNFR2 (hTNFR2) (SEQ ID NO:17). Four cysteine rich domains (CRD) are shown as CRD1, CRD2, CRD3, and CRD4.

FIG. 6 shows an alignment of DcR3 (SEQ ID NO:3) and human OPG (SEQ ID NO:18). Four cysteine rich domains are identified as CRD1, CRD2, CRD3, and CRD4.

FIGS. 12 and 13 illustrate antigen specificity of certain DcR3 antibodies referred to as 4C4.1.4; 5C4.14.7; 11C5.2.8; 8D3.1.5; and 4B7.1.1.

FIGS. 12 and 14 illustrate the results of an ELISA to determine blocking activity of certain DcR3 antibodies referred to as 4C4.1.4; 5C4.14.7; 11C5.2.8; 8D3.1.5; and 4B7.1.1.

DETAILED DESCRIPTION OF THE PREFERRED EMBODIMENTS

I. Definitions

Figure 7:
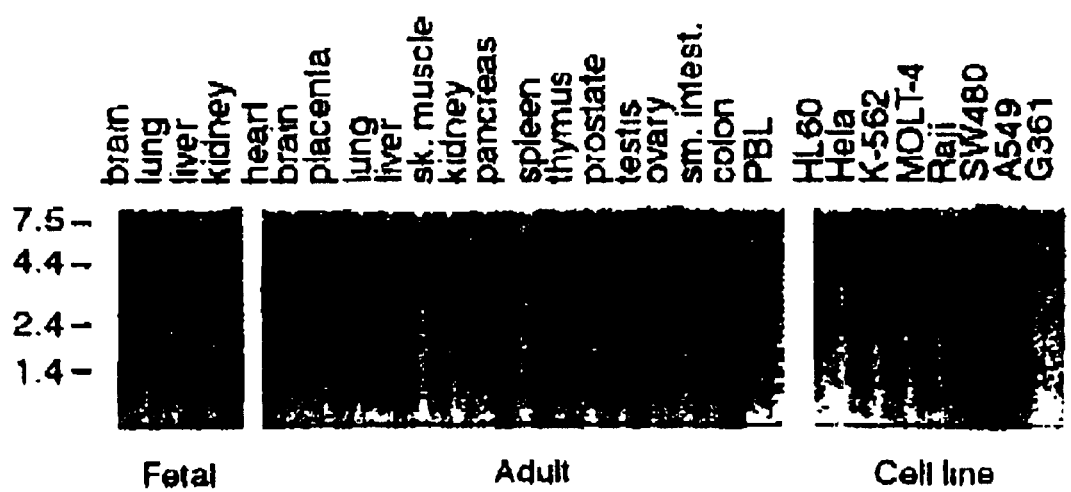
FIG. 7 shows expression of DcR3 mRNA in human tissues and human cancer cell lines as determined by Northern Blot hybridization analysis.

The terms "DcR3 polypeptide" and "DcR3" when used herein encompass native sequence DcR3 and DcR3 variants (which are further defined herein). The DcR3 may be isolated from a variety of sources, such as from human tissue types or from another source, or prepared by recombinant or synthetic methods.

A "native sequence DcR3" comprises a polypeptide having the same amino acid sequence as an DcR3 derived from nature. Such native sequence DcR3 can be isolated from nature or can be produced by recombinant or synthetic means. The term "native sequence DcR3" specifically encompasses naturally-occurring truncated or secreted forms of the DcR3 (e.g., an extracellular domain sequence), naturally-occurring variant forms (e.g., alternatively spliced forms) and naturally-occurring allelic variants of the DcR3. In one embodiment of the invention, the native sequence DcR3 is a mature or full-length native sequence DcR3 comprising amino acids 1 to 300 of FIG. 1 (SEQ ID NO:1). Alternatively, the DcR3 comprises amino acids 1 to 215 of FIG. 1 (SEQ ID NO:1).

"DcR3 variant" means a DcR3 as defined below having at least about 80% amino acid sequence identity with the DcR3 having the deduced amino acid sequence shown in FIG. 1 (SEQ ID NO:1) for a full-length native sequence human DcR3 or the domain sequences identified herein. Such DcR3 variants include, for instance, DcR3 polypeptides wherein one or more amino acid residues are added, or deleted, at the N- or C-terminus of the sequence of FIG. 1 (SEQ ID NO:1) or the domain sequences identified herein. Ordinarily, a DcR3 variant will have at least about 80% amino acid sequence identity, more preferably at least about 90% amino acid sequence identity, and even more preferably at least about 95% amino acid sequence identity with the amino acid sequence of FIG. 1 (SEQ ID NO:1).

"Percent (%) amino acid sequence identity" with respect to the DcR3 sequences identified herein is defined as the percentage of amino acid residues in a candidate sequence that are identical with the amino acid residues in the DcR3 sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared.

"Percent (%) nucleic acid sequence identity" with respect to the DcR3 sequences identified herein is defined as the percentage of nucleotides in a candidate sequence that are identical with the nucleotides in the DcR3 sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared.

The term "epitope tagged" when used herein refers to a chimeric polypeptide comprising DcR3, or a domain sequence thereof, fused to a "tag polypeptide". The tag polypeptide has enough residues to provide an epitope against which an antibody can be made, yet is short enough such that it does not interfere with activity of the DcR3. The tag polypeptide preferably also is fairly unique so that the antibody does not substantially cross-react with other epitopes. Suitable tag polypeptides generally have at least six amino acid residues and usually between about 8 to about 50 amino acid residues (preferably, between about 10 to about 20 residues).

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the DcR3 natural environment will not be present. Ordinarily, however, isolated polypeptide will be prepared by at least one purification step.

An "isolated" DcR3 nucleic acid molecule is a nucleic acid molecule that is identified and separated from at least one contaminant nucleic acid molecule with which it is ordinarily associated in the natural source of the DcR3 nucleic acid. An isolated DcR3 nucleic acid molecule is other than in the form or setting in which it is found in nature. Isolated DcR3 nucleic acid molecules therefore are distinguished from the DcR3 nucleic acid molecule as it exists in natural cells. However, an isolated DcR3 nucleic acid molecule includes DcR3 nucleic acid molecules contained in cells that ordinarily express DcR3 where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single anti-DcR3 monoclonal antibodies (including agonist, antagonist, and neutralizing or blocking antibodies) and anti-DcR3 antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Active" or "activity" for the purposes herein refers to form(s) of DcR3 which retain the biologic and/or immunologic activities of native or naturally-occurring DcR3.

The terms "apoptosis" and "apoptotic activity" are used in a broad sense and refer to the orderly or controlled form of cell death in mammals that is typically accompanied by one or more characteristic cell changes, including condensation of cytoplasm, loss of plasma membrane microvilli, segmentation of the nucleus, degradation of chromosomal DNA or loss of mitochondrial function. This activity can be determined and measured, for instance, by cell viability assays, FACS analysis or DNA electrophoresis, all of which are known in the art.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, blastoma, gastrointestinal cancer, renal cancer, pancreatic cancer, glioblastoma, neuroblastoma, cervical cancer, ovarian cancer, liver cancer, stomach cancer, bladder cancer, hepatoma, breast cancer, colon cancer, colorectal cancer, endometrial cancer, salivary gland cancer, kidney cancer, prostate cancer, vulval cancer, thyroid cancer, hepatic carcinoma, and various types of head and neck cancer.

The terms "treating," "treatment," and "therapy" as used herein refer to curative therapy, prophylactic therapy, and preventative therapy.

The term "mammal" as used herein refers to any mammal classified as a mammal, including humans, cows, horses, dogs and cats. In a preferred embodiment of the invention, the mammal is a human.

II. Compositions and Methods of the Invention

The present invention provides newly identified and isolated nucleotide sequences encoding polypeptides referred to in the present application as DcR3. In particular, Applicants have identified and isolated cDNA encoding a DcR3 polypeptide, as disclosed in further detail in the Examples below. Using BLAST and FastA sequence alignment computer programs, Applicants found that a full-length native sequence DcR3 (shown in FIG. 1 and SEQ ID NO:1) has about 28% amino acid sequence identity with human TNFR2. Accordingly, it is presently believed that DcR3 disclosed in the present application likely is a newly identified member of the TNFR family and may possess activities or properties typical of the TNFR protein family. Like OPG, another TNFR family member, [Simonet et al., supra], the DcR3 molecule presently appears to lack a transmembrane region and may be a secreted polypeptide.

It is presently believed that DcR3 may be a soluble decoy receptor that is capable of binding Fas ligand and/or inhibiting Fas ligand activity, including inhibiting apoptosis induction by Fas ligand. As shown in the Examples below, gene amplification experiments revealed the DcR3 gene is amplified in a considerable number of primary lung and colon cancers, suggesting that certain cancers may escape immune-cytotoxic attack by expressing a decoy receptor such as DcR3 that blocks Fas ligand-induced apoptosis. The Examples also show that DcR3 is capable of immune-inhibitory activity, suggesting its use, for instance, in treating T-cell mediated diseases. Antibodies to DcR3 can be used to sensitize DcR3-producing cancers to immune-cytotoxic attack and to enhance proliferation of tumor-reactive lymphocytes.

B. Modifications of DcR3

Covalent modifications of DcR3 are included within the scope of this invention. One type of covalent modification includes reacting targeted amino acid residues of the DcR3 with an organic derivatizing agent that is capable of reacting with selected side chains or the N- or C-terminal residues of the DcR3. Derivatization with bifunctional agents is useful, for instance, for crosslinking DcR3 to a water-insoluble support matrix or surface for use in the method for purifying anti-DcR3 antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homo-bifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]pro-pioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W. H. Freeman & Co., San Francisco, pp. 79–86 (1983)], acetylation of the N-terminal amine, and amidation of any C-terminal carboxyl group.

Another type of covalent modification of the DcR3 polypeptide included within the scope of this invention comprises altering the native glycosylation pattern of the polypeptide. "Altering the native glycosylation pattern" is intended for purposes herein to mean deleting one or more carbohydrate moieties found in native sequence DcR3, and/or adding one or more glycosylation sites that are not present in the native sequence DcR3.

Addition of glycosylation sites to the DcR3 polypeptide may be accomplished by altering the amino acid sequence. The alteration may be made, for example, by the addition of, or substitution by, one or more serine or threonine residues to the native sequence DcR3 (for O-linked glycosylation sites). The DcR3 amino acid sequence may optionally be altered through changes at the DNA level, particularly by mutating the DNA encoding the DcR3 polypeptide at preselected bases such that codons are generated that will translate into the desired amino acids.

Another means of increasing the number of carbohydrate moieties on the DcR3 polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem.*, vol. 10, pp. 259–306 (1981).

Removal of carbohydrate moieties present on the DcR3 polypeptide may be accomplished chemically or enzymatically or by mutational substitution of codons encoding for amino acid residues that serve as targets for glycosylation. Chemical deglycosylation techniques are known in the art and described, for instance, by Sojar, et al., *Arch. Biochem. Biophys.*, 259:52 (2987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of DcR3 comprises linking the DcR3 polypeptide to one of a variety of non-proteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

The DcR3 of the present invention may also be modified in a way to form a chimeric molecule comprising DcR3 fused to another, heterologous polypeptide or amino acid sequence. In one embodiment, such a chimeric molecule comprises a fusion of the DcR3 with a tag polypeptide which provides an epitope to which an anti-tag antibody can selectively bind. The epitope tag is generally placed at the amino- or carboxyl-terminus of the DcR3. The presence of such epitope-tagged forms of the DcR3 can be detected using an antibody against the tag polypeptide. Also, provision of the epitope tag enables the DcR3 to be readily purified by affinity purification using an anti-tag antibody or another type of affinity matrix that binds to the epitope tag. In an alternative embodiment, the chimeric molecule may comprise a fusion of the DcR3 with an immunoglobulin or a particular region of an immunoglobulin. In particular, the chimeric molecule may comprise an ECD of DcR3 which includes amino acids 1 to 215 of FIG. 1 (SEQ ID NO:1) fused to an IgG molecule. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159–2165 (1988)]; the c-myc tag and the 8F9, 3C7, 6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., *Protein Engineering*, 3(6):547–553 (1990)]. Other tag polypeptides include the Flag-peptide [Hopp et al., *BioTechnology*, 6:1204–4210 (1988)]; the KT3 epitope peptide [Martin et al., *Science*, 255:192–194 (1992)]; an α-tubulin epitope peptide [Skinner et al., *J. Biol. Chem.*, 266:14163–14166 (1991)]; and the T7 gene 10 protein peptide tag [Lutz-Freyermuth et al., *Proc. Natl. Acad. Sci. USA*, 87:6393–6397 (1990)].

C. Preparation of DcR3

The description below relates primarily to production of DcR3 by culturing cells transformed or transfected with a vector containing DcR3 nucleic acid. It is, of course, contemplated that alternative methods, which are well known in the art, may be employed to prepare DcR3. For instance, the DcR3 sequence, or portions thereof, may be produced by direct peptide synthesis using solid-phase techniques [see, e.g., Stewart et al., *Solid-Phase Peptide Synthesis*, W. H. Freeman Co., San Francisco, Calif. (1969); Merrifield, *J. Am. Chem. Soc.*, 85:2149–2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the DcR3 may be chemically synthesized separately and combined using chemical or enzymatic methods to produce the full-length DcR3.

1. Isolation of DNA Encoding DcR3

DNA encoding DcR3 may be obtained from a cDNA library prepared from tissue believed to possess the DcR3 mRNA and to express it at a detectable level. Accordingly, human DcR3 DNA can be conveniently obtained from a cDNA library prepared from human tissue, such as described in the Examples. The DcR3-encoding gene may also be obtained from a genomic library or by oligonucleotide synthesis.

Libraries can be screened with probes (such as antibodies to the DcR3 or oligonucleotides of at least about 20–80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding DcR3 is to use PCR methodology [Sambrook et al., supra; Dieffenbach et al., *PCR Primer; A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as Gen-Bank or other private sequence databases. Sequence identity (at either the amino acid or nucleotide level) within defined regions of the molecule or across the full-length sequence can be determined through sequence alignment using computer software programs such as ALIGN, DNAstar, and INHERIT which employ various algorithms to measure homology.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

DcR3 variants can be prepared by introducing appropriate nucleotide changes into the DcR3 DNA, or by synthesis of the desired DcR3 polypeptide. Those skilled in the art will appreciate that amino acid changes may alter post-translational processes of the DcR3, such as changing the number or position of glycosylation sites or altering the membrane anchoring characteristics.

Variations in the native full-length sequence DcR3 or in various domains of the DcR3 described herein, can be made, for example, using any of the techniques and guidelines for conservative and non-conservative mutations set forth, for instance, in U.S. Pat. No. 5,364,934. Variations may be a substitution, deletion or insertion of one or more codons encoding the DcR3 that results in a change in the amino acid sequence of the DcR3 as compared with the native sequence DcR3. Optionally the variation is by substitution of at least one amino acid with any other amino acid in one or more of the domains of the DcR3 molecule. The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1985); Zoller et al., *Nucl. Acids Res.*, 10:6487 (1982)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the DcR3 variant DNA.

Scanning amino acid analysis can also be employed to identify one or more amino acids along a contiguous sequence which are involved in the interaction with a particular ligand or receptor. Among the preferred scanning amino acids are relatively small, neutral amino acids. Such amino acids include alanine, glycine, serine, and cysteine. Alanine is the preferred scanning amino acid among this group because it eliminates the side-chain beyond the beta-carbon and is less likely to alter the main-chain conformation of the variant. Alanine is also preferred because it is the most common amino acid. Further, it is frequently found in both buried and exposed positions [Creighton, *The Proteins*, (W. H. Freeman & Co., N.Y.); Chothia, *J. Mol. Biol.*, 105:1 (1976)]. If alanine substitution does not yield adequate amounts of variant, an isoteric amino acid can be used.

Once selected DcR3 variants are produced, they can be contacted with, for instance, Fas ligand, and the interaction, if any, can be determined. The interaction between the DcR3 variant and Fas ligand can be measured by an in vitro assay, such as described in the Examples below. While any number of analytical measurements can be used to compare activities and properties between a native sequence DcR3 and a DcR3 variant, a convenient one for binding is the dissociation constant $K_d$ of the complex formed between the DcR3 variant and Fas ligand as compared to the $K_d$ for the native sequence DcR3.

Optionally, representative sites in the DcR3 sequence suitable for mutagenesis (such as deletion of one or more amino acids) would include sites within one or more of the cysteine-rich domains. Such variations can be accomplished using the methods described above.

2. Selection and Transformation of Host Cells

Host cells are transfected or transformed with expression or cloning vectors described herein for DcR3 production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of transfection are known to the ordinarily skilled artisan, for example, $CaPO_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published Jun. 29, 1989. For mammalian cells without such cell walls, the calcium phosphate precipitation method of Graham and van der Eb, *Virology*, 52:456–457 (1978) can be employed. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527–537 (1990) and Mansour et al., *Nature*, 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635).

In addition to prokaryotes, eukaryotic microbes such as filamentous fungi or yeast are suitable cloning or expression hosts for DcR3-encoding vectors. *Saccharomyces cerevisiae* is a commonly used lower eukaryotic host microorganism.

Suitable host cells for the expression of glycosylated DcR3 are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977))Graham et al., *J. Gen Virol.*, 36:59 (1977)); Chinese hamster ovary cells/-DHFR(CHO, Urlaub and Chasin, *Proc. Natl. Acad. Sci. USA*, 77:4216 (1980)) Urlaub and Chasin, *Proc. Natl. Acad. Sci. USA*, 77:4216 (1980)); mouse sertoli cells (TM4, Mather, *Biol. Reprod.*, 23:243–252 (1980) Mather, *Biol. Reprod.*, 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding DcR3 may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The DcR3 may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the DcR3 DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including Saccharomyces and Kluyveromyces α-factor leaders, the latter described in U.S. Pat. No. 5,010,182), or acid phosphatase leader, the *C. albicans* glucoamylase leader (EP 362,179 published Apr. 4, 1990), or the signal described in WO 90/13646 published Nov. 15, 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the $2\mu$ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the DcR3 nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschumper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:23–33 (1977)].

Expression and cloning vectors usually contain a promoter operably linked to the DcR3 nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:617–624 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21–25 (1983)]. Promoters for use in bacterial systems also will contain a Shine-Dalgarno (S.D.) sequence operably linked to the DNA encoding DcR3.

Examples of suitable promoting sequences for use with yeast hosts include the promoters for 3-phosphoglycerate kinase [Hitzeman et al., *J. Biol. Chem.*, 255:12073 (1980)] or other glycolytic enzymes [Hess et al., *Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

DcR3 transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the DcR3 by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the DcR3 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding DcR3.

Still other methods, vectors, and host cells suitable for adaptation to the synthesis of DcR3 in recombinant vertebrate cell culture are described in Gething et al., *Nature*, 293:620–625 (1981); Mantei et al., *Nature*, 281:40–46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201–5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence DcR3 polypeptide or against a synthetic peptide based on the DNA sequences provided herein or against exogenous sequence fused to DcR3 DNA and encoding a specific antibody epitope.

5. Purification of Polypeptide

Forms of DcR3 may be recovered from culture medium or from host cell lysates. If membrane-bound, it can be released from the membrane using a suitable detergent solution (e.g. Triton-X 100) or by enzymatic cleavage. Cells employed in expression of DcR3 can be disrupted by various physical or chemical means, such as freeze-thaw cycling, sonication, mechanical disruption, or cell lysing agents.

It may be desired to purify DcR3 from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the DcR3. Various methods of protein purification may be employed and such methods are known in the art and described for example in Deutscher, *Methods in Enzymology*, 182 (1990); Scopes, *Protein Purification:Principles and Practice*, Springer-Verlag, New York (1982). The purification step(s) selected will depend, for example, on the nature of the production process used and the particular DcR3 produced.

D. Uses for DcR3

Nucleotide sequences (or their complement) encoding DcR3 have various applications in the art of molecular biology, including uses as hybridization probes, in chromosome and gene mapping and in the generation of anti-sense RNA and DNA. DcR3 nucleic acid will also be useful for the preparation of DcR3 polypeptides by the recombinant techniques described herein.

The full-length native sequence DcR3 (FIG. 2; SEQ ID NO:2) gene, or portions thereof, may be used as hybridization probes for a cDNA library to isolate the full-length DcR3 gene or to isolate still other genes (for instance, those encoding naturally-occurring variants of DcR3 or DcR3 from other species) which have a desired sequence identity to the DcR3 sequence disclosed in FIG. 2 (SEQ ID NO:2). Optionally, the length of the probes will be about 20 to about 50 bases. The hybridization probes may be derived from the nucleotide sequence of SEQ ID NO:2 or from genomic sequences including promoters, enhancer elements and introns of native sequence DcR3. By way of example, a screening method will comprise isolating the coding region of the DcR3 gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the DcR3 gene of the present invention can be used to screen libraries of human cDNA, genomic DNA or mRNA to determine which members of such libraries the probe hybridizes to. Hybridization techniques are described in further detail in the Examples below.

The ESTs disclosed and claimed in the present application may similarly be employed as probes, using the methods disclosed herein.

The probes may also be employed in PCR techniques to generate a pool of sequences for identification of closely related DcR3 sequences.

Nucleotide sequences encoding a DcR3 can also be used to construct hybridization probes for mapping the gene which encodes that DcR3 and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries. Example 12 below describes further a selected chromosomal mapping technique and identifies that the DcR3 gene has been mapped to human chromosome 20.

As disclosed herein, the DcR3 gene can be amplified in cancerous cells and tissues. Example 13 below, for instance, describes that the DcR3 gene was found to be amplified in different lung and colon cancers. Accordingly, the molecules of the present invention may be used as diagnostics to detect the presence of cancer or the risk of onset of cancer by analyzing tissue for amplification of the DcR3 gene. Detection of DcR3 gene amplification in patient tissues may also be employed by skilled practitioners in selecting preferred modes of treatment for the patient, such as identifying a mode of anti-DcR3 antibody treatment for the patient. Such diagnostic methods or assays may be conducted using various techniques, including PCR or FISH techniques known in the art. Tissues may also be analyzed using the techniques described in Example 13 for the determination of DcR3 gene amplification.

When the coding sequences for DcR3 encode a protein which binds to another protein (example, where the DcR3 is a receptor), the DcR3 can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor DcR3 can be used to isolate correlative ligand(s). Screening assays can be designed to find lead compounds that mimic the biological activity of a native DcR3 or a ligand or receptor for DcR3. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode DcR3 or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding DcR3 can be used to clone genomic DNA encoding DcR3 in accordance with established techniques and the genomic sequences used to generate transgenic animals that contain cells which express DNA encoding DcR3. Methods for generating transgenic animals, particularly animals such as mice or rats, have become conventional in the art and are described, for example, in U.S. Pat. Nos. 4,736,866 and 4,870,009. Typically, particular cells would be targeted for DcR3 transgene incorporation with tissue-specific enhancers. Transgenic animals that include a copy of a transgene encoding DcR3 introduced into the germ line of the animal at an embryonic stage can be used to examine the effect of increased expression of DNA encoding DcR3. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of DcR3 can be used to construct a DcR3 "knock out" animal which has a defective or altered gene encoding DcR3 as a result of homologous recombination between the endogenous gene encoding DcR3 and altered genomic DNA encoding DcR3 introduced into an embryonic cell of the animal. For example, cDNA encoding DcR3 can be used to clone genomic DNA encoding DcR3 in accordance with established techniques. A portion of the genomic DNA encoding DcR3 can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113–151]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the DcR3 polypeptide.

DcR3, as disclosed in the present specification, can be employed therapeutically to regulate apoptosis by Fas ligand or by another ligand that DcR3 binds to in mammalian cells, as well as to modulate other functions of Fas ligand. This therapy can be accomplished for instance, using in vivo or ex vivo gene therapy techniques. Nucleic acid encoding DcR3 may be used in gene therapy. In gene therapy applications, genes are introduced into cells in order to achieve in vivo synthesis of a therapeutically effective genetic product, for example the replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. [Zamecnik et al., *Proc. Natl. Acad. Sci.*, 83:4143–4146 (1986)]. The oligonucleotides can be modified to enhance their uptake, e.g., by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo, in the cells of the intended host. Techniques suitable for the transfer of nucleic acid into mammalian cells in vitro include the use of liposomes, electroporaton, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection [Dzau et al., *Trends in Biotechnology*, 11:205–210 (1993)]. In some situations, it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.*, 262:4429–4432 (1987) and Wagner et al., *Proc. Natl. Acad. Sci.*, 87:3410–3414 (1990). For a review of gene marking and gene therapy protocols, see Anderson et al., *Science*, 256:808–813 (1992).

It is contemplated that DcR3 polypeptides and modified forms of DcR3 (as well as DcR3 antibodies described below) may be used therapeutically as agonist or antagonist molecules. For instance, DcR3 molecules which can act as antagonists may be used to inhibit or block Fas ligand or Fas ligand induced activity or alternatively, the activity of another ligand that DcR3 binds to. Examples of such forms of DcR3 include the chimeric molecules described above which comprise a fusion of the DcR3 with an immunoglobulin or a particular region of an immunoglobulin. This includes chimeric molecules containing an extracellular domain sequence of DcR3 and an immunoglobulin. These DcR3 molecules, as described herein, can inhibit Fas ligand induced activity, such as Fas ligand induced apoptosis or Fas ligand induced lymphocyte activity, as well as suppress the proliferaton of lymphocytes in response to antigenic stimulation. Based upon the mixed lymphocyte reaction assay data discussed in the Examples, it is believed that the induced immune response need not be exclusively mediated by Fas ligand.

This inhibition or antagonist activity therefore has applications in diseases which are immune mediated and involve, at least as a component of their induction and mechanism, the activation of T lymphocytes which subsequently orchestrate a variety of intra- and inter-cellular events which in these diseases is deleterious to the mammal. Such immune mediated diseases which are believed to involve or rely upon T lymphocyte activation include but are not limited to asthma and other allergic allergic diseases including for example, allergic rhinitis and atopic diseases, rheumatoid arthritis and juvenile chronic arthritis, psoriasis, inflammatory bowel diseases including Crohn's disease and ulcerative colitis, gluten-sensitive enteropathy, and Whipple's disease, multiple sclerosis and other immune mediated demyelinating CNS diseases, and transplant related diseases including graft rejecton and graft-versus-host disease.

These diseases are believed to be immune mediated either directly as for example, by demonstrable ameliorative affect of immunosuppressive therapy in mammals, or indirectly, as for example, by the demonstraton of T or B lymphocytes or auto-antibody within lesions of patients with the disease or through inference of data obtained via the experimental use of animal models of human disease. [See, generally, Samter's Immunological Diseases, 5th Ed., Vols. I and II, Little, Brown and Company (1995)].

Carriers and their formulations are described in *Remington's Pharmaceutical Sciences*, 16th ed., 1980, Mack Publishing Co., edited by Oslo et al. Typically, an appropriate amount of a pharmaceutically-acceptable salt is used in the formulation to render the formulation isotonic. Examples of the carrier include buffers such as saline, Ringer's solution and dextrose solution. The pH of the solution is preferably from about 5 to about 8, and more preferably from about 7.4 to about 7.8. Further carriers include sustained release preparations such as semipermeable matrices of solid hydrophobic polymers, which matrices are in the form of shaped articles, e.g., films, liposomes or microparticles. It will be apparent to those persons skilled in the art that certain carriers may be more preferable depending upon, for instance, the route of administration and concentration of the DcR3 molecule being administered.

Administration to a mammal may be accomplished by injection (e.g., intravenous, intraperitoneal, subcutaneous, intramuscular), or by other methods such as infusion that ensure delivery to the bloodstream in an effective form.

Effective dosages and schedules for administration may be determined empirically, and making such determinations is within the skill in the art.

E. Anti-DcR3 Antibodies

The present invention further provides anti-DcR3 antibodies. Exemplary antibodies include polyclonal, monoclonal, humanized, bispecific, and heteroconjugate antibodies.

1. Polyclonal Antibodies

The DcR3 antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the DcR3 polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The DcR3 antibodies may, alternatively, be monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the DcR3 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.,* 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against DcR3. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

As described in the Examples below, anti-DcR3 monoclonal antibodies have been prepared. Several of these antibodies, referred to as 4C4.1.4; 5C4.14.7; 11C5.2.8; 8D3.1.5; and 4B7.1.1 have been deposited with ATCC and have been assigned deposit accession numbers HB-12573, HB-12574, HB-12572, HB-12571, and HB-12575, respectively, In one embodiment, the monoclonal antibodies of the invention will have the same biological characteristics as one or more of the antibodies secreted by the hybridoma cell lines deposited under accession numbers HB-12573, HB-12574, HB-12572, HB-12571 or HB-12575. The term "biological characteristics" is used to refer to the in vitro and or in vivo activities or properties of the monoclonal antibodies, such as the ability to bind to DcR3 or to substantially block Fas ligand/DcR3 binding. Optionally, the monoclonal antibody will bind to the same epitope as at least one of the antibodies specifically referred to above. Such epitope binding can be determined by conducting various assays, like those described herein and in the examples.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Humanized Antibodies

The DcR3 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–327 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1992); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86–95 (1991)].

4. Bispecific Antibodies

Bispecific antibodies are monoclonal, preferably human or humanized, antibodies that have binding specificities for at least two different antigens. In the present case, one of the binding specificities is for the DcR3, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537–540 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in NO 93/08829, published May 13, 1993, and in Traunecker et al., *EMBO J.*, 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/20373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

F. Uses for DcR3 Antibodies

The DcR3 antibodies of the invention have various utilities. For example, DcR3 antibodies may be used in diagnostic assays for DcR3, e.g., detecting its expression in specific cells, tissues, serum or tumors. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 194:495–496 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

DcR3 antibodies also are useful for the affinity purification of DcR3 from recombinant cell culture or natural sources. In this process, the antibodies against DcR3 are immobilized on a suitable support, such a Sephadex resin or filter paper, using methods well known in the art. The immobilized antibody then is contacted with a sample containing the DcR3 to be purified, and thereafter the support is washed with a suitable solvent that will remove substantially all the material in the sample except the DcR3, which is bound to the immobilized antibody. Finally, the support is washed with another suitable solvent that will release the DcR3 from the antibody.

The DcR3 antibodies of the invention also have therapeutic utility. For example, DcR3 antibodies may be used to antagonize the activity of DcR3 that blocks Fas ligand induced apoptosis or that blocks potential autoimmune/inflammatory effects. DcR3 antagonists can function in cancer therapy by, for instance, preventing DcR3 from inhibiting immune-cytotoxic killing of cancer cells. Such can be accomplished, for example, by blocking Fas ligand-DcR3 binding or by augmenting or enhancing DcR3 clearance or removal. Those skilled in the art will appreciate that there are molecules which can suppress the activation or stimulation of an immune response and thus which have the capacity to cause some level of immunosuppression and thereby have the capacity to assist cancer cells in evading the mammal's immune surveillance system and response. An example of a natural inhibitor of the immune system is CTLA4 which can inhibit T lymphocyte activation by inhibiting a co-stimulation mechanism of T lymphocytes. It has been shown that antagonism of this inhibition in vivo enhances the ability of the mammal to immunologically reject cancer. It has been reported that the blocking of CTLA4 with an antibody in vivo resulted in enhancement of the immune response to an established cancer and causing subsequent rejection of this cancer. [Kwon et al., *Proc. Nat. Acad. Sci.*, 94:8099–8103 (1997); Leach et al., *Science*, 271:1734–1736 (1996)].

Therapeutic compositions and modes of administration (such as described above for DcR3) may be employed. Effective dosages and schedules for administering the antagonist may be determined empirically, and making such determinations is within the skill in the art. Those skilled in the art will understand that the dosage of antagonist that must be administered will vary depending on, for example, the mammal which will receive the antagonist, the route of administration, the particular type of antagonist used and other drugs being administered to the mammal. Guidance in selecting appropriate doses for antibody antagonists is found in the literature on therapeutic uses of antibodies, e.g., *Handbook of Monoclonal Antibodies*, Ferrone et al., eds., Noges Publications, Park Ridge, N.J., (1985) ch. 22 and pp. 303–357; Smith et al., *Antibodies in Human Diagnosis and Therapy*, Haber et al., eds., Raven Press, New York (1977) pp. 365–389. A typical daily dosage of the antagonist used alone might range from about 1 µg/kg to up to 100 mg/kg of body weight or more per day, depending on the factors mentioned above.

In methods of treating cancer using the DcR3 antagonists described herein, it is contemplated that other, additional therapies may be administered to the mammal, and such includes but is not limited to, chemotherapy and radiation therapy, immunoadjuvants, cytokines, and antibody-based therapies. Examples include interleukins (e.g., IL-1, IL-2, IL-3, IL-6), leukemia inhibitory factor, interferons, TGF-beta, erythropoietin, thrombopoietin, HER-2 antibody and anti-CD20 antibody. Other agents known to induce apoptosis in mammalian cells may also employed, and such agents include TNF-α, TNF-β (lymphotoxin-α), CD30 ligand, and 4-1BB ligand.

Chemotherapies contemplated by the invention include chemical substances or drugs which are known in the art and are commercially available, such as Doxorubicin, 5-Fluorouracil, Cytosine arabinoside ("Ara-C"), Cyclophosphamide, Thiotepa, Busulfan, Cytoxin, Taxol, Methotrexate, Cisplatin, Melphalan, Vinblastine and Carboplatin. Preparation and dosing schedules for such chemotherapy may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992). The chemotherapy is preferably administered in a pharmaceutically-acceptable carrier, such as those described above. The antagonist may be administered sequentially or concurrently with the one or more other therapeutic agents. The amounts of antagonist and therapeutic agent depend, for example, on what type of drugs are used, the cancer being treated, and the scheduling and routes of administration but would generally be less than if each were used individually.

Following administration of antagonist to the mammal, the mammal's cancer and physiological condition can be monitored in various ways well known to the skilled practitioner. For instance, tumor mass may be observed physically or by standard x-ray imaging techniques.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Isolation of cDNA Clones Encoding Human DcR3

The extracellular domain (ECD) sequences (including the secretion signal sequence, if any) from about 950 known secreted proteins from the Swiss-Prot public database were used to search EST databases. The EST databases included public EST databases (e.g., GenBank), a private EST database (LIFESEQ™, Incyte Pharmaceuticals, Palo Alto, Calif.), and proprietary ESTs from Genentech. The search was performed using the computer program BLAST or BLAST2 [Altschul et al., *Methods in Enzymology*, 266:460–480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

Using various ESTs, a consensus DNA sequence was assembled. The ESTs included an EST proprietary to Genentech (SEQ ID NO:3; see FIGS. 3 and 4), six ESTs from the private database (SEQ ID NO:4; SEQ ID NO:5; SEQ ID NO:6; SEQ ID NO:7; SEQ ID NO:8; SEQ ID NO:9; see FIG. 4), and an EST from the public database (SEQ ID NO:10).

Based on the consensus sequence, oligonucleotides were synthesized to identify by PCR a cDNA library that contained the sequence of interest and for use as probes to isolate a clone of the full-length coding sequence for DcR3.

```
A pair of PCR primers (forward and reverse) were synthesized:
CACGCTGGTTTCTGCTTGGAG                                         (SEQ ID NO:11)

AGCTGGTGCACAGGGTGTCATG                                        (SEQ ID NO:12)

A probe was also synthesized:
CCCAGGCACCTTCTCAGCCAGCCAGCAGCTCCAGCTCAGAGCAGTGCCAGCCC         (SEQ ID NO:13)
```

In order to screen several libraries for a source of a full-length clone, DNA from the libraries was screened by PCR amplification with the PCR primer pair identified above. A positive library was then used to isolate clones encoding the DcR3 gene using the probe oligonucleotide and one of the PCR primers.

RNA for construction of the cDNA libraries was isolated from fetal lung tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB; PRK5B is a precursor of pRK5D that does not contain the SfiI site; see, Holmes et al., Science, 253:1278–1280 (1991)) in the unique XhoI and NotI sites.

DNA sequencing of the clones isolated as described above gave the full-length DNA sequence for DcR3 (FIG. 2; SEQ ID NO:2) and the derived protein sequence for DcR3 (FIG. 1; SEQ ID NO:1).

The entire nucleotide sequence of DcR3 is shown in FIG. 2 (SEQ ID NO:2). Clone DNA30942 contains a single open reading frame with an apparent translational initiation site at nucleotide positions 101–103 [Kozak et al., supra] (FIG. 2; SEQ ID NO:2). The predicted polypeptide precursor is 300 amino acids long. The N-terminus of the sequence contains a typical secretion signal (amino acids 1–23 of FIG. 1; SEQ ID NO:1). Analysis of the DcR3 amino acid sequence revealed the presence of four CRDs, as shown in FIGS. 5 and 6. It is believed that DcR3 lacks a transmembrane domain. It is also believed that amino acids 1 to 215 of FIG. 1 (SEQ ID NO:1) represents an ECD which includes four CRDs (FIG. 5). DcR3 has one potential N-linked glycosylation site at residue 173 of FIG. 1. Clone DNA30942 has been deposited with ATCC (identified as DNA30942-1134) and is assigned ATCC deposit no. 209254.

Based on a BLAST and FastA sequence alignment analysis of the full-length sequence, DcR3 shows some amino acid sequence identity to TNFR2 (28.7%) and OPG (31%). See FIGS. 5 and 6. All the cysteines in the four CRDs of DcR3 and OPG are conserved; however, the C-terminal portion of DcR3 is approximately 100 residues shorter.

Example 2

Northern Blot Analysis

Expression of DcR3 mRNA in human tissues and human cancer cell lines was examined by Northern blot analysis. Human RNA blots were hybridized to a $^{32}$P-labelled DNA probe based on the full length DcR3 cDNA. Human fetal RNA blot MTN (Clontech), human adult RNA blot MTN-II (Clontech), human cancer cell line blots (Clontech) were incubated with the DNA probes. Blots were then incubated with the probes in hybridization buffer (5×SSPE; 2×Denhardt's solution; 100 mg/mL denatured sheared salmon sperm DNA; 50% formamide; 2% SDS) for 60 hours at 42° C. The blots were washed several times in 2×SSC; 0.05% SDS for 1 hour at room temperature, followed by a 30 minute wash in 0.1×SSC; 0.1% SDS at 50° C. The blots were developed after overnight exposure by phosphorimager analysis (Fuji).

A predominant DcR3 transcript of approximately 1.2 kB was detected in fetal lung, brain, and liver, and in adult spleen, colon, and lung (FIG. 7). In addition, a relatively high DcR3 mRNA level was detected in the human colon carcinoma cell line, SW480 (see FIG. 7).

Example 3

Use of DcR3 as a Hybridization Probe

The following method describes use of a nucleotide sequence encoding DcR3 as a hybridization probe.

DNA comprising the coding sequence of DcR3 (as shown in FIG. 2, SEQ ID NO:2) is employed as a probe to screen for homologous DNAs (such as those encoding naturally-occurring variants of DcR3) in human tissue cDNA libraries or human tissue genomic libraries.

Hybridization and washing of filters containing either library DNAs is performed under the following high stringency conditions. Hybridization of radiolabeled DcR3-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence DcR3 can then be identified using standard techniques known in the art.

Example 4

Expression of DcR3 in E. coli

This example illustrates preparation of DcR3 by recombinant expression in E. coli.

The DNA sequence encoding DcR3 (SEQ ID NO:2) is initially amplified using selected PCR primers. The primers should contain restriction enzyme sites which correspond to the restriction enzyme sites on the selected expression vector. A variety of expression vectors may be employed. An example of a suitable vector is pBR322 (derived from E. coli; see Bolivar et al., Gene, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the DcR3 coding region, lambda transcriptional terminator, and an argU gene.

The ligation mixture is then used to transform a selected E. coli strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized DcR3 protein can then be purified using a metal chelating column under conditions that allow tight binding of the protein.

Example 5

Expression of DcR3 in Mammalian Cells

This example illustrates preparation of DcR3 by recombinant expression in mammalian cells.

A. The vector, pRK5 (see EP 307,247, published Mar. 15, 1989), is employed as the expression vector. Optionally, the DcR3 DNA is ligated into pRK5 with selected restriction enzymes to allow insertion of the DcR3 DNA using ligation methods such as described in Sambrook et al., supra. The resulting vector is called pRK5-DcR3.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-DcR3 DNA is mixed with about 1 μg DNA encoding the VA RNA gene [Thimmappaya et al., Cell, 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of DcR3 polypeptide. The cultures containing transfected cells may undergo further incubation (in serum free medium) and the medium is tested in selected bioassays.

In an alternative technique, DcR3 may be introduced into 293 cells transiently using the dextran sulfate method described by Sompayrac et al., Proc. Natl. Acad. Sci., 78:7575 (1981). 293 cells are grown to maximal density in a spinner flask and 700 ug pRK5-DcR3 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 ug/ml bovine insulin and 0.1 ug/ml bovine transferrin. After about four days, the conditioned media is centrifuged and filtered to remove cells and debris. The sample containing expressed DcR3 can then be concentrated and purified by any selected method, such as dialysis and/or column chromatography.

B. In another embodiment, epitope-tagged DcR3 was expressed in CHO cells. The DcR3 was subcloned out of the pRK5 vector. The subclone insert then undergoes PCR to fuse in frame with a poly-his tag into a Baculovirus expression vector. The poly-his tagged DcR3 insert was then subcloned into a SV40 driven vector containing a selection marker DHFR for selection of stable clones. Finally, the CHO cells were transfected (as described above) with the SV40 driven vector. The culture medium containing the expressed poly-His tagged DcR3 was concentrated and purified by $Ni^{2+}$-chelate affinity chromatography. Analysis of the purified protein by SDS-PAGE revealed that the secreted DcR3 protein has a molecular weight of approximately 35 kDa.

Example 6

Expression of DcR3 in Yeast

The following method describes recombinant expression of DcR3 in yeast.

First, yeast expression vectors are constructed for intracellular production or secretion of DcR3 from the ADH2/GAPDH promoter. DNA encoding DcR3, a selected signal peptide and the promoter is inserted into suitable restriction enzyme sites in the selected plasmid to direct intracellular expression of DcR3. For secretion, DNA encoding DcR3 can be cloned into the selected plasmid, together with DNA encoding the ADH2/GAPDH promoter, the yeast alpha-factor secretory signal/leader sequence, and linker sequences (if needed) for expression of DcR3.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant DcR3 can subsequently be isolated and purified by removing the yeast cells from the fermentation medium by centrifugation and then concentrating the medium using selected cartridge filters. The concentrate containing DcR3 may further be purified using selected column chromatography resins.

Example 7

Expression of DcR3 in Baculovirus

The following method describes recombinant expression of DcR3 in Baculovirus.

The DcR3 is fused upstream of an epitope tag contained with a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the DcR3 or the desired portion of the DcR3 (such as the sequence encoding an extracellular domain, e.g., amino acids 1 to 215 of FIG. 1 (SEQ ID NO:1)) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4–5 days of incubation at 28° C., the released viruses are harvested and used for further amplifications. Viral infection and protein expression is performed as described by O'Reilley et al., Baculovirus expression vectors: A laboratory Manual, Oxford: Oxford University Press (1994).

Expressed poly-his tagged DcR3 can then be purified, for example, by $Ni^{2+}$-chelate affinity chromatography as follows. Extracts are prepared from recombinant virus-infected Sf9 cells as described by Ruppert et al., *Nature*, 362:175–179 (1993). Briefly, Sf9 cells are washed, resuspended in sonication buffer (25 mL Hepes, pH 7.9; 12.5 mM $MgCl_2$; 0.1 mM EDTA; 10% Glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% Glycerol, pH 7.8) and filtered through a 0.45 um filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with (loading buffer, at which point fraction collection is started. Next, the column is washed with a secondary wash buffer (50 mM phosphate; 300 mM NaCl, 10% Glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or western blot with $Ni^{2+}$-NTA-conjugated to alkaline phosphatase (Qiagen). Fractions containing the eluted $His_{10}$-tagged DcR3 are pooled and dialyzed against loading buffer.

Alternatively, purification of the IgG tagged (or Fc tagged) DcR3 can be performed using known chromatography techniques, including for instance, Protein A or protein G column chromatography.

Example 8

Preparation of Antibodies that Bind DcR3

This example illustrates preparation of monoclonal antibodies which can specifically bind DcR3.

Techniques for producing the monoclonal antibodies are known in the art and are described, for instance, in Goding, supra. Immunogens that may be employed include purified DcR3, fusion proteins containing DcR3, and cells expressing recombinant DcR3 on the cell surface. Selection of the immunogen can be made by the skilled artisan without undue experimentation.

Mice, such as Balb/c, are immunized with the DcR3 immunogen emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect DcR3 antibodies.

After a suitable antibody titer has been detected, the animals "positive" for antibodies can be injected with a final intravenous injection of DcR3. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against DcR3. Determination of "positive" hybridoma cells secreting the desired monoclonal antibodies against DcR3 is within the skill in the art.

The positive hybridoma cells can be injected intraperitoneally into syngeneic Balb/c mice to produce ascites containing the anti-DcR3 monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 9

In Vitro Assays to Determine Interaction of DcR3 with Fas Ligand

A. FACS Analysis

An assay was conducted to determine if DcR3 binds to 293 cells transiently transfected with individual TNF family ligands. Human 293 cells (ATCC CRL 1573) were transiently transfected with empty pRK5 vector (see Example 5) or pRK5 encoding full-length TNF-alpha [Pennica et al., *Nature*, 312:724–729 (1984)], Fas ligand [Suda et al., *Cell*, 75:1169–1178 (1993)], LIGHT [Mauri et al., *Immunity*, 8:21 (1998)], Apo-2 ligand [[WO 97/25428 published Jul. 17, 1997)], Apo-3 ligand (also referred to as TWEAK) [Marsters et al., *Current Biology*, 8:525 (1998); Chicheportiche et al., *J. Biol. Chem.*, 272:32401 (1997)], or OPG (also referred to as TRANCE, RANKL) [Wong et al., *J. Biol. Chem.*, 272:25190 (1997); Anderson et al., *Nature*, 390:175 (1997); Lacey et al., *Cell*, 93:165 (1998)]. The cells were then incubated for 1 hour at 37° C. with a recombinant biotinylated Fc-tagged DcR3 (expressed as described in Example 7 above and purified by Protein A chromatography [Ashkenazi et al., *Methods: A Companion to Methods in Enzymology*, 8:104 (1995)], a Fc-tagged ectodomain of TNFR1 (control), or PBS buffer (control). The cells were further incubated for 30 minutes at 37° C. with phycoerythrin-conjugated streptavidin (Gibco BRL) and then analyzed by fluorescence activated cell sorting (FACS).

Figure 8A:
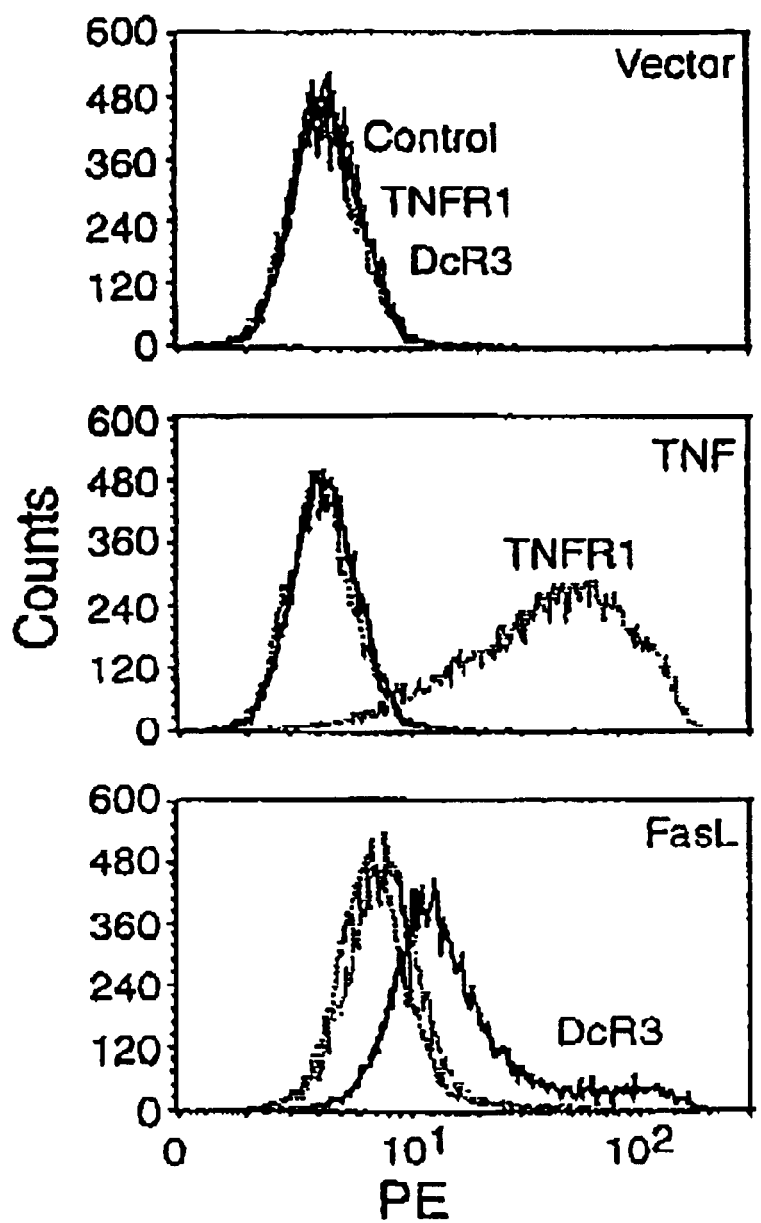
FIG. 8A shows results of a FACS analysis to determine specific binding of DcR3 to Fas ligand.

The results showed that DcR3 specifically bound to Fas ligand transfected cells but not to cells transfected with TNF-alpha (see FIG. 8A). DcR3 also showed significant binding to LIGHT, but did not bind to Apo-2 ligand, Apo-3 ligand, or OPG (data not shown).

B. Co-Immunoprecipitation Assay

A co-immunoprecipitation assay was also conducted to determine if DcR3 binds to a soluble Fas ligand.

Purified, soluble Fas ligand (Alexis Biochemicals) (1 microgram) was incubated for 1 hour at room temperature with the Fc-tagged DcR3 (described above), TNFR1, or Fas ectodomain (5 microgram), and immunoprecipitated with protein A-sepharose (Repligen). Precipitates were resolved by SDS polyacrylamide gel electrophoresis (4–20% gradient) under reducing conditions (25 mM dithiothreitol), and visualized by immunoblot, followed by enhanced chemiluminescence detection (Amersham) with rabbit polyclonal anti-Fas ligand antibody (Oncogene Research Products) at 2 microgram/ml. The soluble Fas ligand itself was also directly loaded for comparison.

Figure 8B:
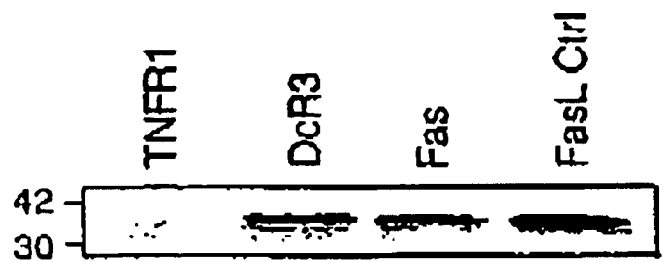
FIG. 8B shows results of a co-immunoprecipitation assay to determine specific binding of DcR3 to soluble Fas ligand.

The results are shown in FIG. 8B. The Fc-tagged DcR3 bound to the purified, soluble Fas ligand, as did Fc-tagged Fas, but not TNFR1. The results suggest that DcR3 is another TNFR family member (besides Fas) that can bind to Fas ligand.

Example 10

In Vitro Assays to Determine Ability of DcR3 to Inhibit Fas Ligand Activity

A. Inhibition of Apoptosis Induction by Transfected Fas Ligand

The effect of DcR3 on apoptosis induction by transient transfection of full length Fas ligand in HeLa cells expressing Fas was examined.

Human HeLa S3 cells (ATCC CCL 22) were transiently transfected with pRK5 (see Example 5), or pRK5-encoding full length Fas ligand [Suda et al., supra] (1 microgram/$10^6$ cells). The transfected cells were incubated at 37° C./5% $CO_2$ in the presence of PBS buffer, Fc-tagged TNFR1, Fc-tagged Fas, or Fc-tagged DcR3 (see Example 9) (50 microgram/ml) for 18 hours. Apoptosis was then analyzed by FACS for determination of annexin binding, as described previously by Marsters et al., *Curr. Biol.*, 6:1669–1676 (1996).

Figure 9A:
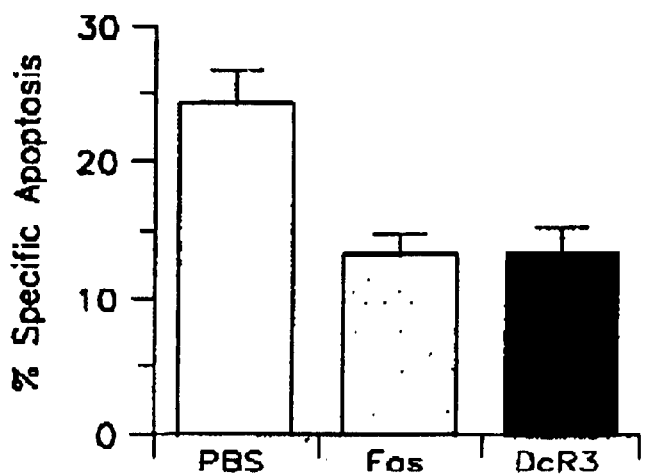
FIGS. 9A–C show the results of in vitro assays to determine inhibition of Fas ligand activity by DcR3.

The results are illustrated in FIG. 9A. The data are means±SEM of triplicates. The Fas ligand induced apoptosis in approximately 25% of the HeLa cells. The Fc-tagged Fas or Fc-tagged DcR3 inhibited this effect significantly, whereas the Fc-tagged TNFR1 did not.

B. Inhibition of T cell AICD

An assay was conducted to determine the effect of DcR3 on T cell AICD, which involves function of endogenous Fas ligand (see Nagata, supra).

CD3+ lymphocytes were isolated from peripheral blood of individual human donors, stimulated with phytohemagglutinin (2 microgram/ml) for 24 hours, and cultured in the presence of IL-2 (100 U/ml) for 5 days (as described previously by Marsters et al., *Curr. Biol.*, supra (1996)). The cells were then plated in wells coated with PBS buffer or anti-CD3 antibody (Ortho Pharmaceuticals), and incubated in the presence of PBS buffer, control IgG, Fc-tagged Fas or Fc-tagged DcR3 (10 microgram/ml) at 37° C./5%$CO_2$. After 18 hours, apoptosis of CD4+ cells was determined by FACS as described in Section A above.

Figure 9B:
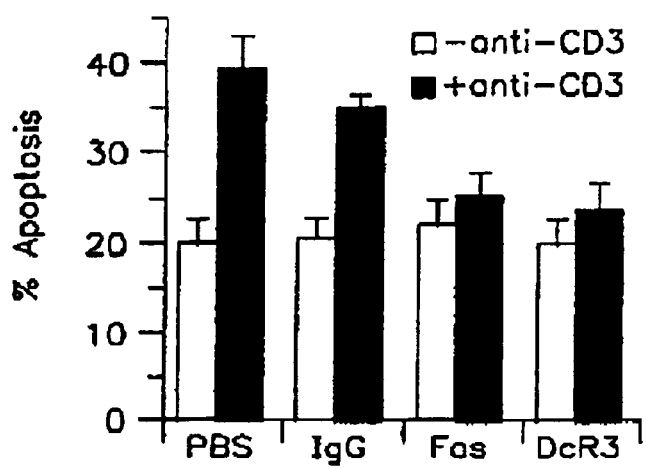

The results are shown in FIG. 9B. The data are means±SEM of results for 5 donors. TCR engagement with anti-CD3 antibody increased the level of apoptosis in IL-2— stimulated CD4+ T cells by approximately 2-fold. See FIG. 9B. Consistent with previous reports [Dhein et al., *Nature*, 373:438 (1995)], Fc-tagged Fas blocked that effect substantially, whereas Fc-tagged DcR3 blocked the induction of apoptosis to a similar extent.

C. Inhibition of Jurkat cell Killing by NK cells

An assay was conducted to determine the effect of DcR3 on killing of Fas-expressing target cells by peripheral blood NK cells, a process that involves Fas ligand function [Arase et al., *J. Exp. Med.*, 181:1235 (1995); Medvedev et al., *Cytokine*, 9:394 (1997)].

NK cells were prepared from peripheral blood of individual donors by enrichment with anti-CD56 magnetic micro-beads (Myltenyi Biotech), and incubated in RPMI 1640/10% FBS media at 37° C./5% $CO_2$ for 24 hours with $^{51}$Cr-loaded Jurkat T leukemia cells at effector to target ratios of 1:1 and 1:5, in the presence of PBS buffer, control IgG, or Fc-tagged Fas or Fc-tagged DcR3 (10 microgram/ml). The level of target cell death was then determined by measuring $^{51}$Cr release in effector-target co-cultures relative to $^{51}$Cr release by detergent lysis of equivalent numbers of Jurkat cells.

Figure 9C:
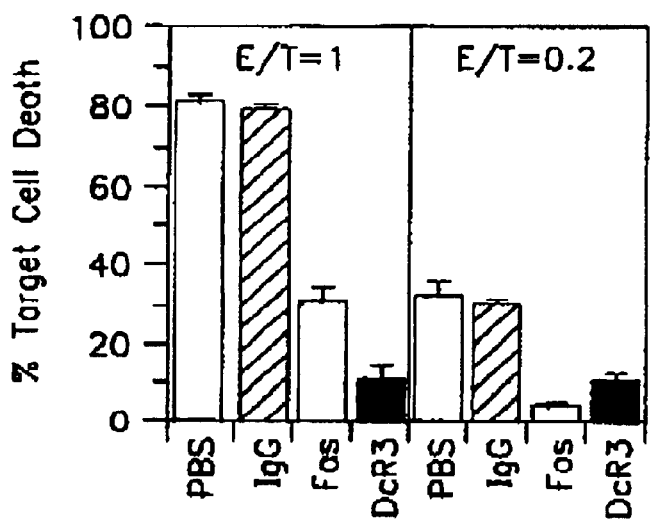
Figure 10A:
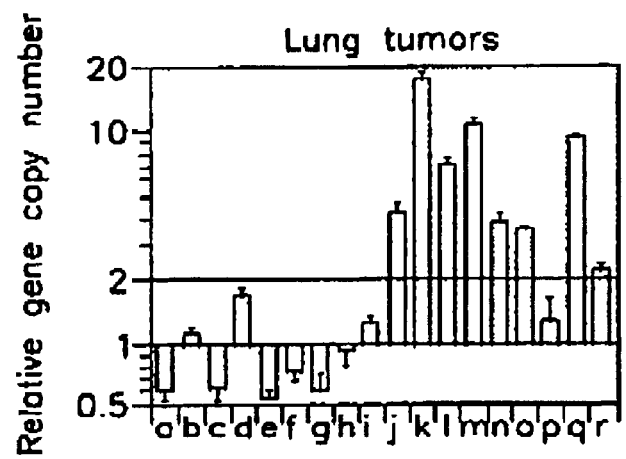
FIGS. 10A–D show the results of assays to determine amplification of the DcR3 gene in various lung and colon tumors and in various colon tumor cell lines.
Figure 10B:
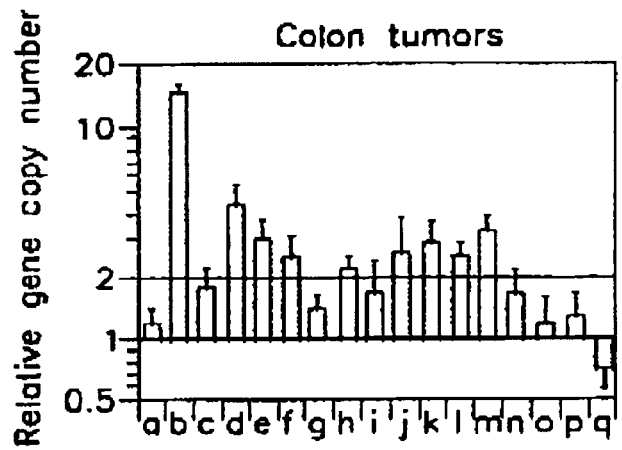
Figure 10C:
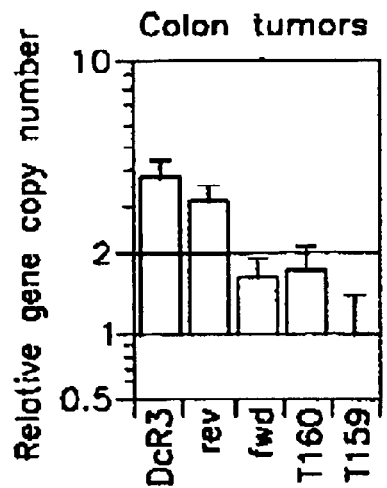
Figure 10D:
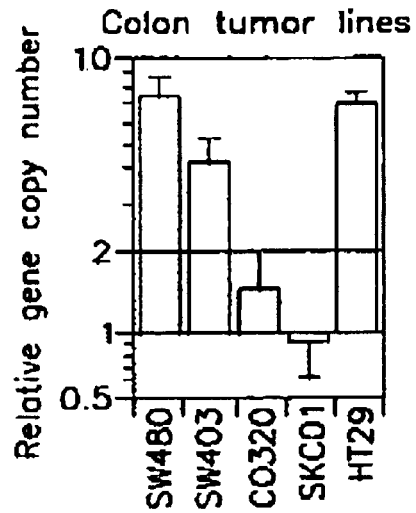

The results are shown in FIG. 9C. The data are means±SD for 2 donors, each assayed in triplicate. NK cells triggered significant cell death in Jurkat T cells. The Fc-tagged Fas and DcR3 inhibited target cell killing substantially, whereas the control IgG did not. The results indicate that binding of DcR3 inhibits Fas ligand activity.

Example 11

Chromosomal Mapping

Chromosomal localization of the human DcR3 gene was examined by radiation hybrid (RH) panel analysis. RH mapping was performed by PCR using a human-mouse cell radiation hybrid panel (Research Genetics) and primers based on the coding region of the DcR3 cDNA [Gelb et al., *Hum. Genet.*, 98:141 (1996)]. Analysis of the PCR data using the Stanford Human Genome Center Database indicates that DcR3 is linked to the marker AFM218xe7, with an LOD of 5.4, and which maps to the distal band of the long arm of human chromosome 20 (20q13).

Example 12

Gene Amplification Assay

This example shows that the DcR3-encoding gene is amplified in the genome of lung and colon cancers. Amplification is associated with overexpression of the gene product, indicating that the DcR3 polypeptide is a useful target for therapeutic intervention in certain cancers. Such therapeutic agents may take the form of antagonists of DcR3-encoding genes, for example, murine-human chimeric, humanized or human antibodies against DcR3.

The starting material for the screen was genomic DNA isolated (using Qiagen reagents) from primary tumor tissue of lung and colon cancers and tumor cell lines. The DNA was quantitated fluorometrically using Hoechst dye 33258 intercalation fluorimetry. As a normalization control, DNA was isolated from peripheral blood leukocytes of 10 normal healthy individuals, which was pooled and used as assay controls for the gene copy in healthy individuals ("NorHu").

The 5' nuclease assay (TaqMan™) and real-time quantitative PCR (Gelmini et al., Clin. Chem., 43:752–758 (1997); ABI Prizm 7700 Sequence Detection System™, Perkin Elmer, Applied Biosystems Division, Foster City, Calif.) were used to determine the relative DcR3 gene copy number in each and whether the DNA encoding DcR3 is over-represented in any of the lung and colon cancers that were screened. The primary lung tumor surgical specimens were provided by the University of Iowa, and the primary colon tumor specimens were provided by the University of Leeds. The panel of lung tumor tissues included 8 adenocarcinomas, 7 squamous cell carcinomas, 1 non small cell carcinoma, 1 small cell carcinoma, and 1 bronchial adenocarcinoma. The panel of colon tumor tissues included 17 adenocarcinomas. The cancer cell lines were obtained from ATCC: SW480 colon adenocarcinoma (ATCC CCL 228); COLO320DM adenocarcinoma (ATCC CCL 220); SK-CO-1 adenocarcinoma (ATCC HTB 39); SW403 adenocarcinoma (ATCC CCL 230); and HT29 colon adenocarcinoma.

The results are reported as relative gene copy numbers, as determined from Delta Ct units. One Delta Ct unit corresponds to 1 PCR cycle or approximately a 2-fold amplification relative to normal; two units correspond to 4-fold; 3 units correspond to 6-fold etc. Quantitation was obtained using primers and a TaqMan™ fluorescent probe derived from the DcR3-encoding gene. Regions of DcR3 which are most likely to contain unique nucleic acid sequences and which are least likely to have spliced out introns are preferred for the primer derivation, e.g., 3'-untranslated region. The sequences for the primers and probes used for the DcR3 gene amplification were as follows:

the Taq DNA polymerase enzyme in a template-dependent manner. The resultant probe fragments disassociate in solution, and signal from the release reporter dye is free from the quenching effect of the second fluorophore. One molecule of reporter dye is liberated for each new molecule synthesized, and detection of the unquenched reporter dye provides the basis for quantitative interpretation of the data.

The 5' nuclease procedure is run on a real-time quantitative PCR device like the ABI Prizm 7700™ Sequence Detection System. The system consists of a thermocycler, laser, charge-coupled device (CCD) camera, and computer. The system amplifies samples in a 96-well format on a thermocycler. During amplification, laser-induced fluorescent signal is collected in real-time through fiber optics cables for all 96 wells, and detected at the CCD. The system includes software for running the instrument and analyzing the data.

5' nuclease assay data are initially expressed as Ct, or the threshold cycle. This is defined as the cycle at which the reporter signal accumulates above the background level of fluorescence. The Ct values are used as quantitative measurement of the relative number of starting copies of a particular target sequence in a nucleic acid sample.

The results are shown in FIG. 10. Eight of the 18 lung tumors, and 9 of the 17 colon tumors showed genomic amplification of DcR3, ranging from 2 to 18 fold (see FIG. 10). To verify the result, colon tumor DNAs were analyzed by quantitative PCR with 3 additional independent sets of DcR3-based primers and probes. Essentially the same amplification was observed (data not shown).

The gene amplification analysis of the human colon tumor cell lines revealed that 3 of 5 cell lines showed significant genomic amplification of DcR3 (FIG. 10), consistent with the amplification of DcR3 in the primary tumor tissues.

The amplification level of the DcR3-flanking regions was also analyzed. A human genomic clone that carries DcR3 was isolated from a bacterial artificial chromosome (BAC) library (Genome Systems). The amplification of the flanking regions from the BAC (68374rev and 68374fwd) was determined, along with the amplification level of the two nearest available genomic markers, AFM218xe7 (T160) and SHGC-36268 (T159) (which maps approximately 500 kb from AFM218xe7) in the colon tumor panel.

DcR3 showed the highest amplification, followed by 68374rev, then by 68374fwd and T160, which showed about the same degree of amplification, whereas T159 showed no

```
hu.DcR3.TMP (probe)           ACACGATGCGTGCTCCAAGCAGAA   (SEQ ID NO:14)

hu.DcR3.TMF (forward primer)  CTTCTTCGCGCACGCTG          (SEQ ID NO:15)

hu.DcR3.TMR (reverse primer)  ATCACGCCGGCACCAG           (SEQ ID NO:16)
```

The 5' nuclease assay reaction is a fluorescent PCR-based technique which makes use of the 5' exonuclease activity of Taq DNA polymerase enzyme to monitor amplification in real time. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the probe is cleaved by amplification (FIG. 10). The results suggest that DcR3 may be at the epicenter of a chromosome 20 region that is amplified in cancer, consistent with the possibility that DcR3 may promote tumor survival.

Example 13

Mixed Lymphocyte Reaction (MLR) Assay to Determine Inhibition Activity by DcR3

MLR assays were conducted to evaluate CD4+ T lymphocyte function by testing the ability of T lymphocytes to proliferate in response to the presentation of allo-antigen. In the "one-way" MLR assay, the donor population of peripheral blood mononuclear cells (PBMCs) is challenged with an irradiated stimulator population of PBMCs. MLR protocols are described in Coligan et al., *Current Protocols in Immunology*, publ. John Wiley & Sons, Inc. (1994). The assay results then identify the molecules which can either enhance or inhibit the proliferation of the responder T lymphocytes in response to stimulation with the presented allo-antigen.

A. MLR Assay of Human PBMCs

PBMCs were isolated from two human donors using standard leukophoresis methods. One donor is used to supply the stimulator PBMCs and the other donor's cells are used to supply the responder PBMCs. The respective cell preparations are then frozen in 50% fetal bovine serum and 50% DMSO until the assay was conducted.

The cells were then thawed overnight in assay medium at 37° C./5%$CO_2$. The assay medium contained RPMI media; 10% fetal bovine serum; 1% penicillin/streptomycin; 1% glutamine; 1% HEPES; 1% non-essential amino acids and 1% pyruvate. After washing, the cells were resuspended in assay medium to a concentration of $3 \times 10^6$ cells/ml. The donor cells being employed as the stimulator cells were irradiated using approximately 3000 Rads.

The PBMC cells were plated (in triplicate) in culture plate wells as follows: 100 microliter of test sample (Fc-tagged DcR3, described in Example 9 above, used at concentrations of 2, 40, 1000 and 25,000 ng/ml as determined by O.D.) diluted to 1% or to 0.1%; 50 microliter of irradiated stimulator cells; 50 microliter of responder PBMC cells. 100 microliter of cell culture media or 100 microliter of CD4-IgG was used as a control. The culture plates were then incubated at 37° C./$CO_2$ for 4 days. On day 5, each well was pulsed with tritiated thymidine (1 micro-Curie/well; Amersham). After 6 hours, the cells were washed 3 times and evaluated by scintillation counting for uptake of the label.

Figure 11A:
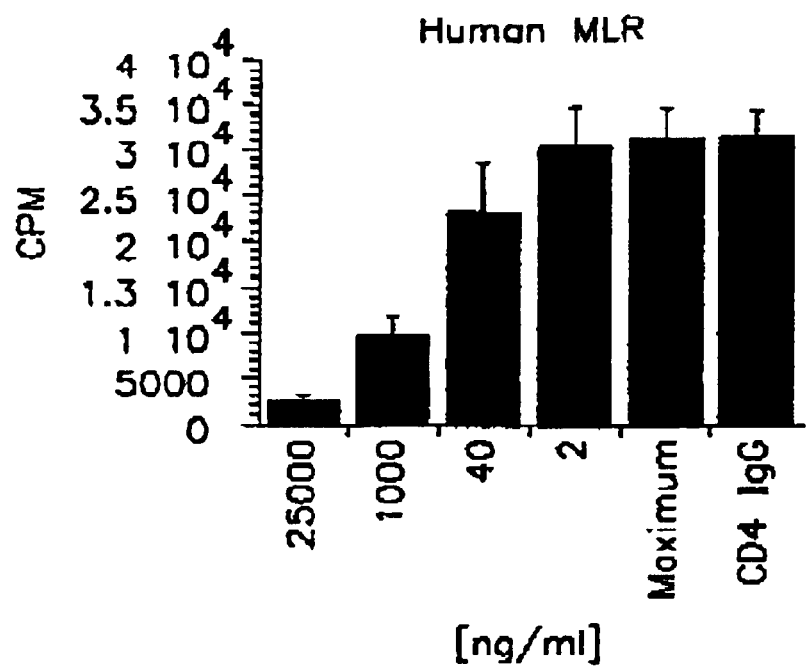
FIGS. 11A–11C show the results of assays to determine the effect of DcR3 on induction of lymphocyte proliferation in mixed lymphocyte reaction (MLR) or co-stimulation assays.

The results are illustrated in FIG. 11A. The data in FIG. 11A illustrates that there is a dose-dependent inhibitory effect of DcR3-IgG on the response of T lymphocytes in the human MLR. As the level of DcR3-IgG was increased from 2 ng/ml to 25,000 ng/ml in the reaction media, there was a significant reduction in T lymphocyte proliferation as shown by the reduced uptake of the tritiated thymidine label when DcR3-IgG was added at either 40, 1000 or 25,000 ng/ml. This inhibition of the MLR was dose dependent and was significant compared to a positive control and to the effect of a control IgG fusion protein (CD4-IgG) which had no effect on the MLR.

B. MLR Assay of Murine PBMCs

PBMCs were isolated from the spleens of two different strains of mice, Balb/c and C57B6. Cells were teased from the freshly harvested spleens and placed into assay media (as described in Section A above). The PBMCs were then isolated by overlaying the cells onto Lympholyte M™ (Organon Teknika), and centrifuging at 2000 rpm for 20 minutes. The mononuclear cell layer was collected and washed in assay media, and resuspended in assay media to a concentration of $1 \times 10^7$ cells/ml. One donor was used to supply the stimulator PBMCs and the other donor's cells were used to supply the responder PBMCs.

The donor cells being employed as the stimulator cells were irradiated using approximately 3000 Rads. The PBMC cells were plated (in triplicate) in culture plate wells as follows: 100 microliter of test sample (Fc-tagged DcR3, used at concentrations of 25, 250, 2500, and 25,000 ng/ml as determined by O.D.) diluted to 1% or to 0.1%; 50 microliter of irradiated stimulator cells; 50 microliter of responder PBMC cells. 100 microliter of cell culture media or 100 microliter of CD4-IgG was used as a control. The culture plates were then incubated at 37° C./5% $CO_2$ for 4 days. On day 5, each well was pulsed with tritiated thymidine (1 micro-Curie/well; Amersham). After 6 hours, the cells were washed 3 times and evaluated by scintillation counting for uptake of the label.

Figure 11B:
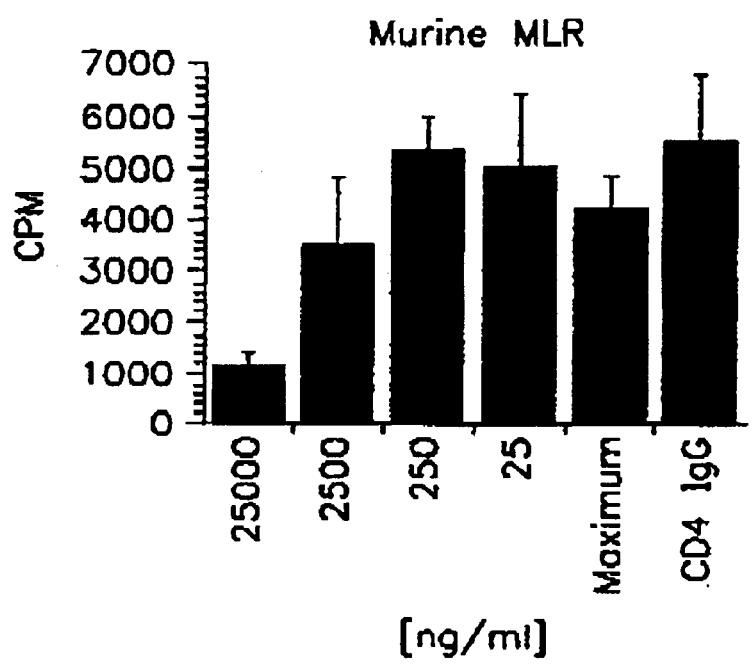

The results are illustrated in FIG. 11B. The data in FIG. 11B illustrate that there is a dose dependent inhibitory effect of DcR3-IgG on the response of T lymphocytes in the murine MLR. As the level of DcR3-IgG was increased from 25 ng/ml to 25,000 ng/ml in the reaction media, there was a significant reduction in T lymphocyte proliferation as shown by the reduced uptake of the tritiated thymidine label. This inhibition of the MLR was dose dependent and was significant compared to a positive control and to the effect of a control IgG fusion protein (CD4-IgG) which had no effect on the MLR.

C. Co-Stimulation Assay

PBLs were isolated from human donors using standard leukophoresis methods. The cell preparations were then frozen in 50% fetal bovine serum and 50% DMSO until the assay was conducted.

The cells were then thawed overnight in assay medium at 37° C./5%$CO_2$. The assay medium contained RPMI media; 10% fetal bovine serum; 1% penicillin/streptomycin; 1% glutamine; 10 mM HEPES; and 50 microgram/ml Gentamycin. After washing, the cells were resuspended in assay medium and incubated at 37° C./5% $CO_2$ overnight.

To prepare the culture plates, 96 well flat bottom plates (Nunc) were coated with murine anti-human CD3 (purchased from Amac) or murine anti-human CD28 (purchased from Biodesign) or both the anti-CD3 and anti-CD28 antibodies. Both antibodies were diluted in Hyclone D-PBS without calcium and magnesium. The anti-CD3 antibody was added at a concentration of 10 ng/well and the anti-CD28 antibody was added at a concentration of 25 ng/well in a total volume of 100 microliter/well. The plates were incubated overnight in PBS at 4° C.

The coated plates were then washed twice with PBS. The washed PBLs were resuspended in media to a concentration of $1 \times 10^6$ cells/ml and added to the plates at 100 microliter/well. Next, 100 microliter of test sample (Fc-tagged DcR3, used at concentrations of 25, 250, 2500, and 25,000 ng/ml as determined by O.D.) or control was added to each well to make a total volume of 200 microliter in each well. 100 microliter of cell culture media or 100 microliter of CD4-IgG was used as a control. The culture plates were then incubated at 37° C./5% $CO_2$ for 72 hours. Subsequently, each well was pulsed with tritiated thymidine (1 micro-Curie/well; Amersham). After 6 hours, the cells were washed 3 times and evaluated by scintillation counting for uptake of the label.

Figure 11C:
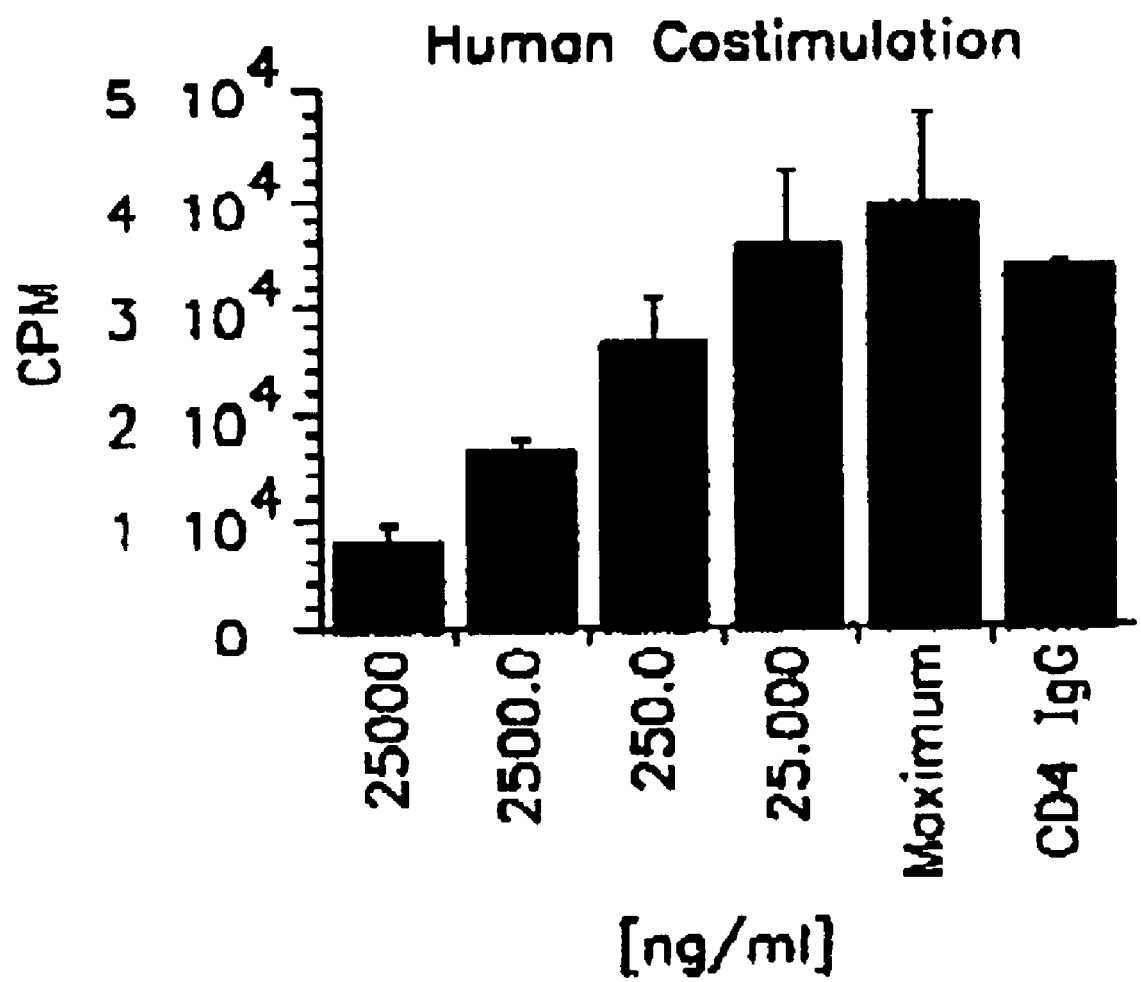

The results are illustrated in FIG. 11C. The data in FIG. 11C illustrates that there is a dose-dependent inhibitory effect of DcR3-IgG on the response of T lymphocytes in the human co-stimulation assay. As the level of DcR3-IgG was increased from 25 ng/ml to 25,000 ng/ml in the reaction media, there was a significant reduction of T lymphocyte proliferation as shown by the reduced uptake of the tritiated thymidine label. This inhibition of the human co-stimulation assay was dose dependent, and was significant compared to a positive control and to the effect of a control IgG fusion protein (CD4-IgG) which had no effect on the human co-stimulation assay.

Example 14

Preparation of Monoclonal Antibodies for DcR3

Balb/c mice (obtained from Charles River Laboratories) were immunized by injecting 0.5 µg/50 µl of an DcR3 immunoadhesin protein (diluted in MPL-TDM adjuvant purchased from Ribi Immunochemical Research Inc., Hamilton, Mont.) 11 times into each hind foot pad at 1 week day intervals. The DcR3 immunoadhesin protein was generated by fusing amino acid residues 1–300 of DcR3 (FIG. 1) to the hinge and Fc region of human immunoglobulin $G_1$ heavy chain in pRK5 as described previously [Ashkenazi et al., Proc. Natl. Acad. Sci., 88:10535–10539 (1991)]. The immunoadhesin protein was expressed in insect cells, and purified by protein A affinity chromatography, as described by Ashkenazi et al., supra.

Three days after the final boost, popliteal lymph nodes were removed from the mice and a single cell suspension was prepared in DMEM media (obtained from Biowhitakker Corp.) supplemented with 1% penicillin-streptomycin. The lymph node cells were then fused with murine myeloma cells P3X63AgU.1 (ATCC CRL 1597) using 35% polyethylene glycol and cultured in 96-well culture plates. Hybridomas resulting from the fusion were selected in HAT medium. Ten days after the fusion, hybridoma culture supernatants were screened in an ELISA to test for the presence of monoclonal antibodies binding to the DcR3 immunoadhesin protein or to CD4-IgG protein.

In the capture ELISA, 96-well microtiter plates (Maxisorb; Nunc, Kamstrup, Denmark) were coated by adding 50 µl of 2 µg/ml goat anti-human IgG Fc (purchased from Cappel Laboratories) in PBS to each well and incubating at 40° C. overnight. The plates were then washed three times with wash buffer (PBS containing 0.05% Tween 20). The wells in the microtiter plates were then blocked with 200 µl of 2.0% bovine serum albumin in PBS and incubated at room temperature for 1 hour. The plates were then washed again three times with wash buffer.

After the washing step, 50 µl of 0.4 µg/ml DcR3 immunoadhesin protein (as described above) in assay buffer (PBS containing 0.5% BSA and 0.5% Tween 20) was added to each well. The plates were incubated for 1 hour at room temperature on a shaker apparatus, followed by washing three times with wash buffer.

Following the wash steps, 100 µl of the hybridoma supernatants or purified antibody (using Protein G-sepharose columns) was added to designated wells in assay buffer. 100 µl of P3X63AgU.1 myeloma cell conditioned medium was added to other designated wells as controls. The plates were incubated at room temperature for 1 hour on a shaker apparatus and then washed three times with wash buffer.

Next, 50 µl HRP-conjugated goat anti-mouse IgG Fc (purchased from Cappel Laboratories), diluted 1:1000 in assay buffer, was added to each well and the plates incubated for 1 hour at room temperature on a shaker apparatus. The plates were washed three times with wash buffer, followed by addition of 50 µl of substrate (TMB microwell peroxidase substrate, Kirkegaard & Perry, Gaithersburg, Md.) to each well and incubation at room temperature for 10 minutes. The reaction was stopped by adding 50 µl of TMB 1-component stop solution (diethyl glycol, Kirkegaard & Perry) to each well, and absorbance at 450 nm was read in an automated microtiter plate reader.

Of the hybridoma supernatants screened in the ELISA, 17 supernatants tested positive (calculated as approximately 4 times above background). The selected hybridomas were tested in an ELISA (described below) for their ability to block the binding of DcR3 to Fas ligand. The potential blocking and non-blocking secreting hybridomas were cloned twice by limiting dilution.

Example 15

ELISA Assay to Determine the Specificity of DcR3 Antibodies

An ELISA was conducted to determine if the monoclonal antibodies described in Example 14 were able to bind other known receptors beside DcR3. Specifically, the 4C4.1.4; 11C5.2.8; 8D3.1.5; 5C4.14.7; and 4B7.1.1 antibodies, respectively, were tested for binding to the DcR3 described herein and to DR4 [Pan et al., supra], DR5 [Sheridan et al., supra and Pan et al., supra], DcR1 [Sheridan et al., supra], and OPG [Simonet et al., supra]. The ELISA was performed essentially as described in Example 14 above. Antigen specificity was determined using 10 microgram/ml of DcR3 antibody.

Figure 13:
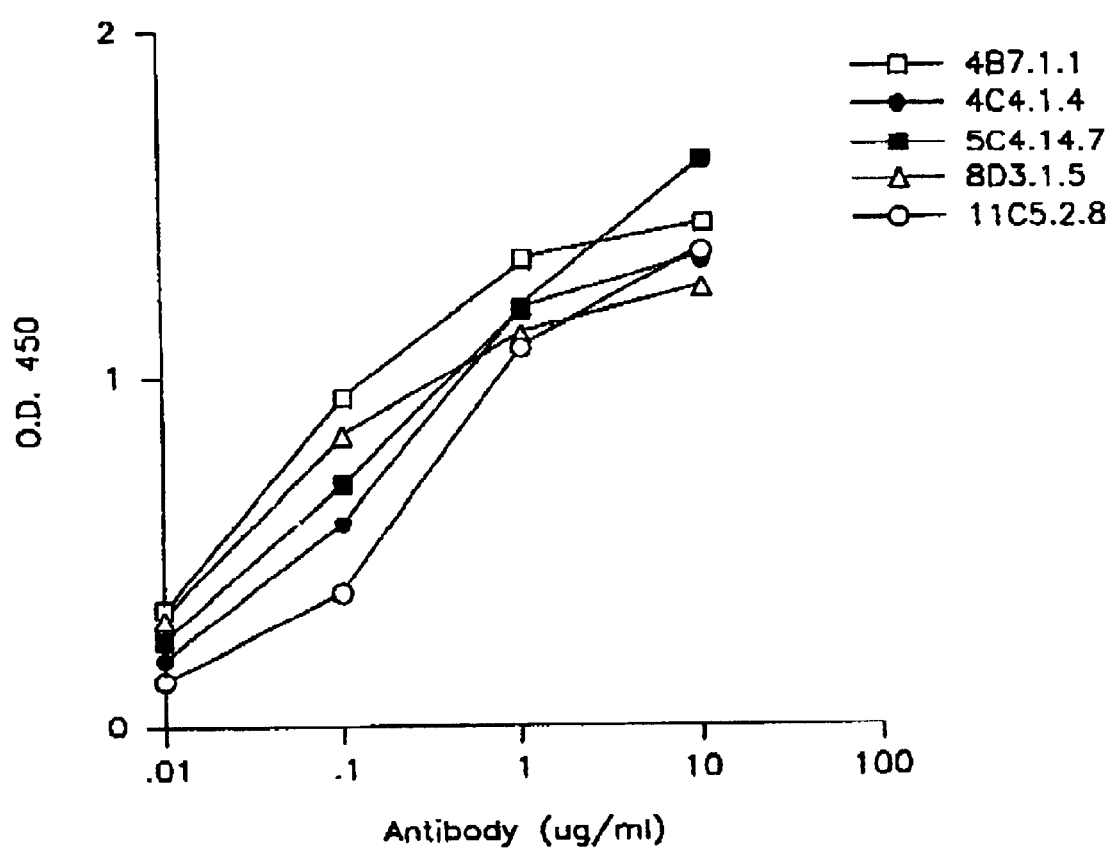

The results are shown in FIG. 12. All five of the DcR3 antibodies bound specifically to DcR3. (see also FIG. 13) None of the five DcR3 antibodies showed cross-reactivity with the other receptors in the assay.

Example 16

ELISA Testing to Determine Blocking Activity of DcR3 Antibodies

In the ELISA, 96-well microtiter plates (Maxisorb; Nunc, Kamstrup, Denmark) were coated by adding 50 µl of 2 µg/ml goat anti-human IgG Fc (purchased from Cappel Laboratories) in carbonate buffer to each well and incubating at 4° C. overnight. The plates were then washed three times with wash buffer (PBS containing 0.05% Tween 20). The wells in the microtiter plates were then blocked with 200 µl of 2.0% bovine serum albumin in PBS and incubated at room temperature for 1 hour. The plates were then washed again three times with wash buffer.

After the washing step, 100 ul of 0.5 ug/ml DcR3 immunoadhesin protein (as described in Example 14 above) or Fas-IgG in assay buffer (PBS containing 0.5% BSA and 0.5% Tween 20) was added to each well. The plates were incubated for 1 hour at room temperature on a shaker apparatus, followed by washing three times with wash buffer.

Following the wash steps, 100 µl of the purified antibodies 4C4.1.4; 11C5.2.8; 8D3.1.5; 5C4.14.7; or 4B7.1.1 was added to designated wells in assay buffer. The plates were incubated at room temperature for 1 hour and then washed three times with wash buffer.

Next, 100 µl Flag tagged Fas ligand (Alexis Pharmaceuticals) (at a concentration of 35 ng/ml), was added to each well and the plates incubated for 1 hour at room temperature. The plates were washed three times with wash buffer, followed by addition of 100 µl of HRP-streptavidin (Zymed) at 1:2000 dilution to the wells for a 1 hour incubation. The plates were again washed three times with wash buffer. Next, 50 µl TMB substrate (TMB microwell peroxidase substrate, Kirkegaard & Perry, Gaithersburg, Md.) was added to each well and incubation at room temperature for 5 minutes. The reaction was stopped by adding 50 µl of TMB 1-component stop solution (diethyl glycol, Kirkegaard & Perry) to each well, and absorbance at 450 nm was read in an automated microtiter plate reader.

Figure 14:
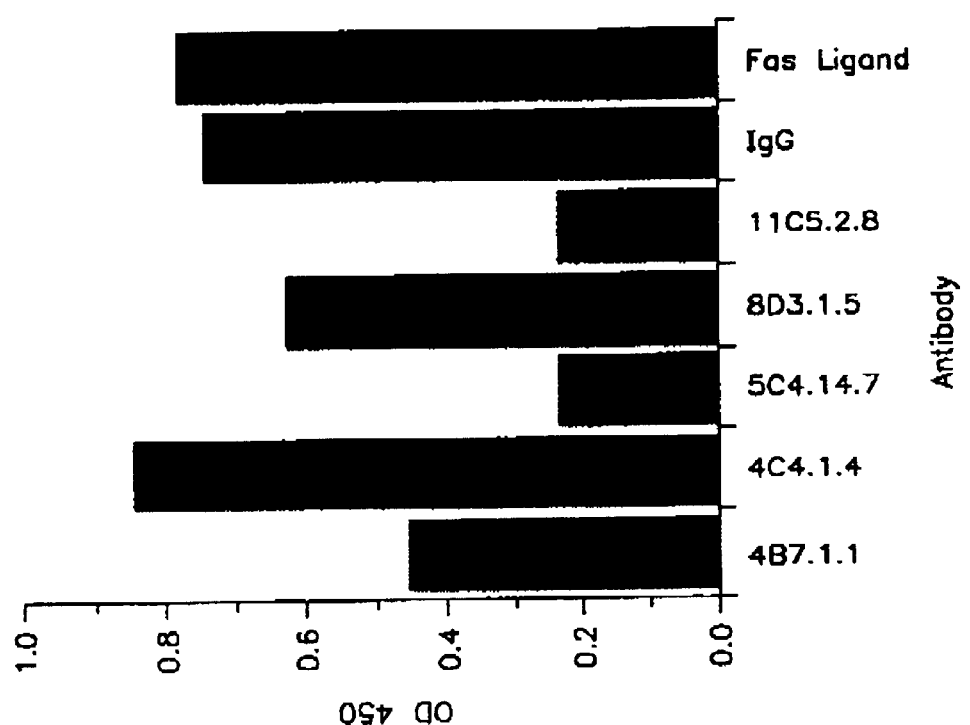

The results are shown in FIG. 12. % blocking activity was determined at 100 fold excess of DcR3 antibody to Fas ligand. Three of the antibodies, 4B7.1.1; 11C5.2.8; and 5C4.14.7, exhibited significant blocking activity. (see also FIG. 14)

Example 17

Antibody Isotyping

The isotype of the DcR3 antibodies (as described above in Examples 14–16) was determined by coating microtiter plates with isotype specific goat anti-mouse Ig (Fisher Biotech, Pittsburgh, Pa.) overnight at 4° C. The plates were then washed with wash buffer (as described in Example 14 above). The wells in the microtiter plates were then blocked with 200 ul of 2% bovine serum albumin (BSA) and incubated at room temperature for one hour. The plates were washed again three times with wash buffer. Next, 100 ul of hybridoma culture supernatant or 5 ug/ml of purified antibody was added to designated wells. The plates were incubated at room temperature for 30 minutes and then 50 ul HRP-conjugated goat anti-mouse IgG (as described above in Example 14) was added to each well. The plates were incubated for 30 minutes at room temperature. The level of HRP bound to the plate was detected using HRP substrate as described above.

The isotyping analysis showed that the 8D3.1.5; 11C5.2.8 and 4B7.1.1 antibodies are IgG1 antibodies. The analysis also showed that the 5C4.14.7 antibody is an IgG2b antibody and that the 4C4.1.4 antibody is an IgG2a antibody. These results are also shown in FIG. 12.

Deposit of Material

The following materials have been deposited with the American Type Culture Collection, 10801 University Blvd., Manassas, Va. USA (ATCC):

| Material | ATCC Dep. No. | Deposit Date |
|---|---|---|
| DNA30942-1134 | 209254 | Sep. 16, 1997 |
| 4C4.1.4 | HB-12573 | Sep. 18, 1998 |
| 5C4.14.7 | HB-12574 | Sep. 18, 1998 |
| 11C5.2.8 | HB-12572 | Sep. 18, 1998 |
| 8D3.1.5 | HB-12571 | Sep. 18, 1998 |
| 4B7.1.1 | HB-12575 | Sep. 18, 1998 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated anti-DcR3 antibody which (a) binds to a DcR3 polypeptide consisting of amino acids 1 to 215 or amino acids 1 to 300 of FIG. 1 (SEQ ID NO:1) and (b) inhibits binding of Fas ligand to the DcR3 polypeptide of (a).

2. The antibody of claim 1 wherein said antibody further inhibits binding of LIGHT ligand to the DcR3 polypeptide of (a).

3. The antibody of claim 1 wherein said antibody is a monoclonal antibody.

4. The antibody of claim 3 wherein said antibody is a chimeric antibody.

5. The antibody of claim 3 wherein said antibody comprises a Fab fragment.

6. The antibody of claim 3 wherein said antibody is a monovalent antibody.

7. The antibody of claim 3 wherein said antibody is a human antibody.

8. The antibody of claim 3 wherein said antibody is expressed in a recombinant host cell selected from the group consisting of a CHO cell, yeast cell and *E. coli*.

9. An isolated anti DcR3 antagonist antibody which (a) binds to a DcR3 polypeptide consisting of amino acids 1 to 215 or amino acids 1 to 300 of FIG. 1 (SEQ ID NO:1), (b) blocks binding of Fas ligand to the DcR3 polypeptide of (a), and (c) neutralizes inhibitory effect of the DcR3 polypeptide of (a) on Fas ligand activity in one or more mammalian cells.

10. The antibody of claim 9 wherein said antibody neutralizes inhibitory effect of the DcR3 polypeptide of (a) on Fas ligand-induced apoptosis in one or more mammalian cells.

11. The antibody of claim 10 wherein said antibody neutralizes inhibitory effect of the DcR3 polypeptide of (a) on Fas ligand-induced apoptosis in one or more mammalian cancer cells.

12. The antibody of claim 11 wherein said mammalian cancer cells are colon cancer cells or lung cancer cells.

13. The antibody of claim 9 wherein said antibody is a monoclonal antibody.

14. The antibody of claim 13 wherein said antibody is a chimeric antibody.

15. The antibody of claim 13 wherein said antibody comprises a Fab fragment.

16. The antibody of claim 13 wherein said antibody is a monovalent antibody.

17. The antibody of claim 13 wherein said antibody is a human antibody.

18. The antibody of claim 13 wherein said antibody is expressed in a recombinant host cell selected from the group consisting of a CHO cell, yeast cell and *E. coli*.

19. The hybridoma cell line 4C4.1.4 deposited as ATCC accession number HB-12573.

20. The hybridoma cell line 5C4.14.7 deposited as ATCC accession number HB-12574.

21. The hybridoma cell, line 11C5.2.8 deposited as ATCC accession number HB-12572.

22. The hybridoma cell line 8D3.1.5 deposited as ATCC accession number HB-12571.

23. The hybridoma cell line 4B7.1.1 deposited as ATCC accession number HB-12575.

24. The 4C4.1.4 monoclonal antibody produced by the hybridoma cell line deposited as ATCC accession number HB-12573.

25. The 5C4.14.7 monoclonal antibody produced by the hybridoma cell line deposited as ATCC accession number HB-12574.

26. The 11C5.2.8 monoclonal antibody produced by the hybridoma cell line deposited as ATCC accession number HB-12572.

27. The 8D3.1.5 monoclonal antibody produced by the hybridoma cell line deposited as ATCC accession number HB-12571.

28. The 4B7.1.1 monoclonal antibody produced by the hybridoma cell line deposited as ATCC accession number HB-12575.

29. An isolated anti-DcR3 antibody which binds to a DcR3 polypeptide comprising amino acids 1 to 215 of FIG. 1 (SEQ ID NO:1) and binds to the same DcR3 polypeptide epitope as the epitope to which the 4C4.1.4 monoclonal antibody produced by the hybridoma cell line deposited as ATCC accession number HS-12573 binds.

30. An isolated anti-DcR3 antibody which binds to a DcR3 polypeptide comprising amino acids 1 to 215 of FIG. 1 (SEQ ID NO:1) and binds to the same DcR3 polypeptide epitope as the epitope to which the 5C4.14.7 monoclonal antibody produced by the hybridoma cell line deposited as ATCC accession number HB-12574 binds.

31. An isolated anti-DcR3 antibody which binds to a DcR3 polypeptide comprising amino acids 1 to 215 of FIG. 1 (SEQ ID NO:1) and binds to the same DcR3 polypeptide epitope as the epitope to which the 11C5.2.8 monoclonal antibody produced by the hybridoma cell line deposited as ATCC accession number HB-12572 binds.

32. An isolated anti-DcR3 antibody which binds to a DcR3 polypeptide comprising amino acids 1 to 215 of FIG. 1 (SEQ ID NO:1) and binds to the same DcR3 polypeptide epitope as the epitope to which the 8D3.1.5 monoclonal antibody produced by the hybridoma cell line deposited as ATCC accession number HB-12571 binds.

33. An isolated anti-DcR3 antibody which binds to a DcR3 polypeptide comprising amino acids 1 to 215 of FIG. 1 (SEQ ID NO:1) and binds to the same DcR3 polypeptide epitope as the epitope to which the 4B7.1.1 monoclonal antibody produced by the hybridoma cell line deposited as ATCC accession number HB-12575 binds.

* * * * *

UNITED STATES PATENT AND TRADEMARK OFFICE
CERTIFICATE OF CORRECTION

PATENT NO. : 6,764,679 B2
DATED : July 20, 2004
INVENTOR(S) : Ashkenazi et al.

It is certified that error appears in the above-identified patent and that said Letters Patent is hereby corrected as shown below:

<u>Column 58,</u>
Line 28, "ATCC accession number HS-12573 binds" should read
-- ATCC accession number HB- 12573 binds. --

Signed and Sealed this

First Day of February, 2005

JON W. DUDAS
*Director of the United States Patent and Trademark Office*